(12) United States Patent
Sowden et al.

(10) Patent No.: US 8,807,979 B2
(45) Date of Patent: Aug. 19, 2014

(54) MACHINE FOR THE MANUFACTURE OF DOSAGE FORMS UTILIZING RADIOFREQUENCY ENERGY

(75) Inventors: Harry S. Sowden, Glenside, PA (US);
Frank J. Bunick, Randolph, NJ (US);
Joseph R. Luber, Quakertown, PA (US);
Leo B. Kriksunov, Ithaca, NY (US);
Christopher E. Szymczak, Marlton, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 447 days.

(21) Appl. No.: 12/887,569

(22) Filed: Sep. 22, 2010

(65) Prior Publication Data
US 2011/0068511 A1 Mar. 24, 2011

Related U.S. Application Data

(60) Provisional application No. 61/245,315, filed on Sep. 24, 2009, provisional application No. 61/255,582, filed on Oct. 28, 2009, provisional application No. 61/314,629, filed on Mar. 17, 2010, provisional application No. 61/358,167, filed on Jun. 24, 2010.

(51) Int. Cl.
*B29C 35/12* (2006.01)
*B29C 43/04* (2006.01)
(Continued)

(52) U.S. Cl.
CPC .............. *A61J 3/06* (2013.01); *A61K 9/2086* (2013.01); *A61K 9/2068* (2013.01); *B30B 11/027* (2013.01); *B30B 15/34* (2013.01); *A61K 9/288* (2013.01); *A61K 9/2095* (2013.01); *A61K 9/2031* (2013.01); *B29C 2035/0861* (2013.01); *A61K 9/2853* (2013.01); *A61K 9/0056* (2013.01); *B30B 11/022* (2013.01); *A61K 9/0058* (2013.01); *B30B 11/10* (2013.01)
USPC ......... 425/174.6; 425/353; 425/354; 264/449

(58) Field of Classification Search
None
See application file for complete search history.

(56) References Cited

U.S. PATENT DOCUMENTS 2,183,053 A 12/1939 Taylor
2,887,437 A 5/1959 Klioze et al.
(Continued)

FOREIGN PATENT DOCUMENTS

CN 1141589 A 1/1997
CN 1498080 A 5/2004
(Continued)

OTHER PUBLICATIONS

U.S. Appl. No. 13/718,357, filed Dec. 18, 2012—Pending.
(Continued)

*Primary Examiner* — Benjamin Schiffman
(74) *Attorney, Agent, or Firm* — William E. McGowan

(57) ABSTRACT

The present invention features the present invention features a machine for the production of a solid dosage form including: (a) a die platen having one or more forming cavities each having an inner wall, a first opening at the surface of one side of the die platen, and a second opening at the surface on the opposite side of the die platen; (b) one or more first forming tools each adapted to move into one of the forming cavities through the first opening of the forming cavity; (c) one or more second forming tools each adapted to move adjacent to one of the second openings or into one of the forming cavities through the second opening of the forming cavity; (d) at least one first RF electrode operably associated with the one or more first forming tools, the one or more second forming tools, or the inner wall of the one or more forming cavities; and (e) at least one second RF electrode operably associated with the one or more first forming tools.

27 Claims, 18 Drawing Sheets

(51) Int. Cl.

| | | |
|---|---|---|
| *B29C 43/06* | (2006.01) | |
| *B29C 43/08* | (2006.01) | |
| *A61K 9/20* | (2006.01) | |
| *B30B 11/02* | (2006.01) | |
| *B30B 15/34* | (2006.01) | |
| *A61J 3/06* | (2006.01) | |
| *A61K 9/28* | (2006.01) | |
| *A61K 9/00* | (2006.01) | |
| *A61K 9/68* | (2006.01) | |
| *B30B 11/10* | (2006.01) | |
| *B29C 35/08* | (2006.01) | |

(56) References Cited

U.S. PATENT DOCUMENTS

| | | |
|---|---|---|
| 3,337,116 A | 8/1967 | Nowak |
| 3,670,065 A | 6/1972 | Eriksson et al. |
| 3,885,026 A | 5/1975 | Heinemann et al. |
| 4,158,411 A | 6/1979 | Hall et al. |
| 4,173,626 A | 11/1979 | Dempski et al. |
| 4,230,693 A | 10/1980 | Izzo et al. |
| 4,260,596 A | 4/1981 | Mackles |
| 4,268,238 A | 5/1981 | Marc |
| 4,268,465 A | 5/1981 | Suh et al. |
| 4,327,076 A | 4/1982 | Puglia et al. |
| 4,398,634 A | 8/1983 | McClosky |
| 4,508,740 A | 4/1985 | McSweeney |
| 4,526,525 A | 7/1985 | Oiso et al. |
| 4,590,075 A | 5/1986 | Wei et al. |
| 4,609,543 A | 9/1986 | Morris et al. |
| 4,642,903 A | 2/1987 | Davies |
| 4,684,534 A | 8/1987 | Valentine |
| 4,758,439 A | 7/1988 | Godfrey |
| 4,762,719 A | 8/1988 | Forester |
| 4,824,681 A | 4/1989 | Schobel et al. |
| 4,828,845 A | 5/1989 | Zamudio-Tena et al. |
| 4,832,956 A | 5/1989 | Gergely et al. |
| 4,851,226 A | 7/1989 | Julian et al. |
| 4,857,331 A | 8/1989 | Shaw et al. |
| 4,863,742 A | 9/1989 | Panoz et al. |
| 4,906,478 A | 3/1990 | Valentine et al. |
| 4,979,720 A | 12/1990 | Robinson |
| 4,980,170 A | 12/1990 | Schneider et al. |
| 4,984,240 A | 1/1991 | Keren-Zvi et al. |
| 4,994,260 A | 2/1991 | Kallstrand et al. |
| 5,013,557 A | 5/1991 | Tai |
| 5,046,618 A | 9/1991 | Wood |
| 5,064,656 A | 11/1991 | Gergely et al. |
| 5,073,374 A | 12/1991 | McCarty |
| 5,075,114 A | 12/1991 | Roche |
| 5,082,436 A | 1/1992 | Choi et al. |
| 5,112,616 A | 5/1992 | McCarty |
| 5,126,151 A | 6/1992 | Bodor et al. |
| 5,134,260 A | 7/1992 | Piehler et al. |
| 5,139,407 A | 8/1992 | Kim et al. |
| 5,178,878 A | 1/1993 | Webling et al. |
| 5,215,755 A | 6/1993 | Roche et al. |
| 5,223,264 A | 6/1993 | Webling et al. |
| 5,262,171 A | 11/1993 | Login et al. |
| 5,275,822 A | 1/1994 | Valentine et al. |
| 5,286,497 A | 2/1994 | Hendrickson et al. |
| 5,304,055 A | 4/1994 | Van Lengerich et al. |
| 5,320,848 A | 6/1994 | Geyer et al. |
| 5,330,763 A | 7/1994 | Gole et al. |
| 5,464,632 A | 11/1995 | Cousin et al. |
| 5,476,667 A * | 12/1995 | Kristensen et al. ............ 424/489 |
| 5,489,436 A | 2/1996 | Hoy et al. |
| 5,501,858 A | 3/1996 | Fuisz |
| 5,501,861 A | 3/1996 | Makimo et al. |
| 5,503,846 A | 4/1996 | Wehling et al. |
| 5,558,880 A | 9/1996 | Gole et al. |
| 5,558,899 A | 9/1996 | Kuzee et al. |
| 5,560,963 A | 10/1996 | Tisack |
| 5,587,172 A | 12/1996 | Cherukuri et al. |
| 5,587,179 A | 12/1996 | Gergely et al. |
| 5,607,697 A | 3/1997 | Alkire et al. |
| 5,622,719 A | 4/1997 | Myers et al. |
| 5,631,023 A | 5/1997 | Kearney et al. |
| 5,635,210 A | 6/1997 | Allen, Jr. et al. |
| 5,648,093 A | 7/1997 | Gole et al. |
| 5,653,993 A | 8/1997 | Ghanta et al. |
| 5,662,849 A | 9/1997 | Bogne et al. |
| 5,672,364 A | 9/1997 | Kato et al. |
| 5,720,974 A | 2/1998 | Makino et al. |
| 5,738,874 A * | 4/1998 | Conte et al. ............ 424/472 |
| 5,814,339 A | 9/1998 | Prudhoe |
| 5,853,758 A * | 12/1998 | Lo ............ 424/464 |
| 5,886,081 A | 3/1999 | Sternowski |
| 5,891,474 A * | 4/1999 | Busetti et al. ............ 424/490 |
| 5,912,013 A | 6/1999 | Rudnic et al. |
| 5,939,091 A | 8/1999 | Eoga et al. |
| 5,997,905 A | 12/1999 | McTeigue et al. |
| 6,024,981 A | 2/2000 | Khankarti et al. |
| 6,060,078 A | 5/2000 | Lee |
| 6,083,531 A * | 7/2000 | Humbert-Droz et al. ..... 424/464 |
| 6,103,260 A | 8/2000 | Luber et al. |
| 6,183,778 B1 * | 2/2001 | Conte et al. ............ 424/472 |
| 6,224,905 B1 | 5/2001 | Lawrence et al. |
| 6,228,398 B1 | 5/2001 | Devane et al. |
| 6,258,381 B1 | 7/2001 | Luber et al. |
| 6,270,805 B1 | 8/2001 | Chen et al. |
| 6,277,409 B1 | 8/2001 | Luber et al. |
| 6,284,270 B1 | 9/2001 | Lagoviyer et al. |
| 6,287,596 B1 | 9/2001 | Murakami et al. |
| 6,316,026 B1 | 11/2001 | Tatara et al. |
| 6,322,819 B1 | 11/2001 | Barnside et al. |
| 6,326,873 B1 * | 12/2001 | Faria ............ 335/251 |
| 6,328,994 B1 | 12/2001 | Shimizu et al. |
| 6,465,010 B1 | 10/2002 | Lagoviyer et al. |
| 6,483,978 B1 * | 11/2002 | Gao et al. ............ 385/135 |
| 6,499,984 B1 | 12/2002 | Ghebre-Sellassie et al. |
| 6,569,463 B2 | 5/2003 | Patel et al. |
| 6,589,554 B1 | 7/2003 | Mizumoto et al. |
| 6,596,311 B1 * | 7/2003 | Dobetti ............ 424/464 |
| 6,612,826 B1 * | 9/2003 | Bauer et al. ............ 425/135 |
| 6,649,888 B2 | 11/2003 | Ryan et al. |
| 6,753,009 B2 | 6/2004 | Luber et al. |
| 6,767,200 B2 | 7/2004 | Sowden et al. |
| 6,814,978 B2 | 11/2004 | Bunick et al. |
| 6,932,979 B2 | 8/2005 | Gergely et al. |
| 7,070,825 B2 | 7/2006 | Ndife et al. |
| 7,157,100 B2 | 1/2007 | Doshi et al. |
| 7,749,533 B2 * | 7/2010 | Fu et al. ............ 424/464 |
| 7,815,937 B2 * | 10/2010 | Mezaache et al. ............ 424/465 |
| 8,127,516 B2 | 3/2012 | Lee et al. |
| 8,182,850 B2 * | 5/2012 | Garcin et al. ............ 426/74 |
| 8,603,525 B2 * | 12/2013 | Oury et al. ............ 424/472 |
| 2001/0033831 A1 | 10/2001 | Chow et al. |
| 2002/0012701 A1 | 1/2002 | Kolter et al. |
| 2002/0018800 A1 | 2/2002 | Pinney et al. |
| 2002/0079121 A1 | 6/2002 | Ryan et al. |
| 2002/0122822 A1 | 9/2002 | Bunick et al. |
| 2002/0186952 A1 * | 12/2002 | Gao et al. ............ 385/135 |
| 2003/0021842 A1 | 1/2003 | Lagoviyer et al. |
| 2003/0068373 A1 | 4/2003 | Luber et al. |
| 2003/0124184 A1 * | 7/2003 | Mezaache et al. ............ 424/465 |
| 2003/0161879 A1 | 8/2003 | Ohmori et al. |
| 2003/0175339 A1 | 9/2003 | Bunick et al. |
| 2003/0194442 A1 | 10/2003 | Guivarch et al. |
| 2003/0224044 A1 | 12/2003 | Weibel |
| 2003/0228368 A1 | 12/2003 | Wynn et al. |
| 2003/0232081 A1 * | 12/2003 | Doshi et al. ............ 424/472 |
| 2004/0115305 A1 | 6/2004 | Andersen et al. |
| 2004/0137057 A1 | 7/2004 | Sowden et al. |
| 2004/0156902 A1 | 8/2004 | Lee et al. |
| 2004/0191499 A1 | 9/2004 | Hallett et al. |
| 2005/0013857 A1 * | 1/2005 | Fu et al. ............ 424/464 |
| 2005/0019407 A1 | 1/2005 | Sowden et al. |
| 2005/0138899 A1 | 6/2005 | Draisey et al. |
| 2005/0142188 A1 | 6/2005 | Gilis et al. |
| 2005/0186274 A1 | 8/2005 | Kohlrausch |
| 2005/0238711 A1 * | 10/2005 | Lambotte et al. ............ 424/464 |
| 2006/0034927 A1 | 2/2006 | Casadevall et al. |

(56) References Cited

U.S. PATENT DOCUMENTS

| | | | |
|---|---|---|---|
| 2006/0134195 A1 | 6/2006 | Fu et al. | |
| 2007/0184111 A1 | 8/2007 | Harris et al. | |
| 2007/0196477 A1 | 8/2007 | Withiam et al. | |
| 2007/0281009 A1 | 12/2007 | Kamisono et al. | |
| 2008/0008742 A1* | 1/2008 | Cherukuri | 424/439 |
| 2008/0286340 A1 | 11/2008 | Andersson et al. | |
| 2009/0029028 A1* | 1/2009 | Garcin et al. | 426/648 |
| 2009/0060983 A1 | 3/2009 | Bunick et al. | |
| 2009/0092672 A1 | 4/2009 | Venkatesh et al. | |
| 2009/0110716 A1 | 4/2009 | Bunick et al. | |
| 2009/0220642 A1* | 9/2009 | Boghani et al. | 426/5 |
| 2009/0311320 A1* | 12/2009 | Oury et al. | 424/465 |
| 2010/0008865 A1* | 1/2010 | Fayet et al. | 424/43 |
| 2011/0068511 A1 | 3/2011 | Sowden et al. | |
| 2011/0071184 A1 | 3/2011 | Bunick et al. | |
| 2011/0268779 A1* | 11/2011 | Canham | 424/401 |

FOREIGN PATENT DOCUMENTS

| | | |
|---|---|---|
| CN | 101052373 A | 10/2007 |
| EP | 0 070 127 | 1/1983 |
| EP | 0192460 B1 | 8/1986 |
| EP | 0 416 791 A2 | 3/1991 |
| EP | 0829341 A2 | 3/1998 |
| EP | 1974724 A2 | 10/2008 |
| EP | 2308511 B1 | 12/2012 |
| GB | 772 315 | 4/1957 |
| GB | 1 097 207 | 12/1967 |
| GB | 1538280 A * | 1/1979 |
| JP | 59 067006 A | 4/1984 |
| JP | 62/205009 A | 3/1986 |
| JP | 649482 B | 6/1994 |
| JP | 1999033084 A | 2/1999 |
| WO | WO 91/12881 | 9/1991 |
| WO | WO 92/06679 | 4/1992 |
| WO | WO 93/13758 A1 | 7/1993 |
| WO | WO 94/06416 | 3/1994 |
| WO | WO 95/09044 A1 | 4/1995 |
| WO | WO 97/38679 A2 | 10/1997 |
| WO | WO 98/32426 A1 | 7/1998 |
| WO | WO 99/17771 | 4/1999 |
| WO | WO 99/44580 A1 | 9/1999 |
| WO | WO 00/04281 | 1/2000 |
| WO | 02/47607 | 6/2002 |
| WO | WO 03/059327 A1 | 7/2003 |
| WO | WO 03/061399 A1 | 7/2003 |
| WO | WO 03/101431 A1 | 12/2003 |
| WO | WO 2004/000197 A2 | 12/2003 |
| WO | WO 2004/046296 A1 | 6/2004 |
| WO | 2004/100857 A2 | 11/2004 |
| WO | WO 2006/127618 | 11/2006 |
| WO | WO 2007/042153 A1 | 4/2007 |
| WO | 2007/125545 A2 | 11/2007 |
| WO | WO 2008/005318 A2 | 1/2008 |
| WO | 2008/015221 A2 | 2/2008 |
| WO | WO 2008/015221 A2 | 2/2008 |
| WO | 2007/125545 A2 | 11/2008 |
| WO | WO 2007/125545 A2 | 11/2008 |
| WO | WO 2009/037319 A2 | 3/2009 |
| WO | WO 2009/080022 A1 | 7/2009 |
| WO | WO 2010/058218 A1 | 5/2010 |
| WO | 2012/039788 A1 | 3/2012 |
| WO | WO 2012/039788 A1 | 3/2012 |

OTHER PUBLICATIONS

Int'l. Search Report for Application No. PCT/US2008/081496, dated Jul. 15, 2009.
Int'l. Search Report for Application No. PCT/US2008/74375, dated Nov. 17, 2008.
Int'l. Search Report for Application No. PCT/US2010/049909 dated Dec. 3, 2010.
Int'l. Search Report for Application No. PCT/US2010/049925 dated Dec. 8, 2010.
Int'l. Search Report for Application No. PCT/US2010/049931 dated Jan. 7, 2011.
Int'l. Search Report for Application No. PCT/US2010/049933 dated Feb. 15, 2011.
Int'l. Search Report for Application No. PCT/US2010/049964 dated Dec. 30, 2010.
Int'l Search Report for Application No. PCT/US2010/049971 dated Jan. 7, 2011.
U.S. Appl. No. 11/847,444, filed Aug. 30, 2007—Pending.
U.S. Appl. No. 12/570,046, filed Sep. 30, 2009—Pending.
U.S. Appl. No. 12/260,151, filed Oct. 29, 2008—Pending.
U.S. Appl. No. 12/566,078, filed Sep. 24, 2009—Pending.
U.S. Appl. No. 12/566,096, filed Sep. 24, 2009—Pending.
U.S. Appl. No. 12/887,544, filed Sep. 22, 2010—Pending.
U.S. Appl. No. 12/887,552, filed Sep. 22, 2010—Pending.
U.S. Appl. No. 12/887,560, filed Sep. 22, 2010—Pending.
U.S. Appl. No. 12/887,564, filed Sep. 22, 2010—Pending.
U.S. Appl. No. 12/887,569, filed Sep. 22, 2010—Pending.
U.S. Appl. No. 12/887,575, filed Sep. 22, 2010—Pending.
U.S. Appl. No. 12/887,582, filed Sep. 22, 2010—Pending.
U.S. Appl. No. 12/887,593, filed Sep. 22, 2010—Pending.
Rambali, B., et al., International Journal of Pharmaceutics 220 (2001), pp. 129-140.
Radio Frequency Company, Microwave, (Feb. 19, 2004), pp. 1-2.
U.S. Appl. No. 13/052,316, filed Mar. 21, 2011—Pending.
U.S. Appl. No. 13/052,219, filed Mar. 21, 2011—Pending.
U.S. Appl. No. 13/052,200, filed Mar. 21, 2011—Pending.
U.S. Appl. No. 13/246,884, filed Sep. 28, 2011—Pending.
Dielectric Heating with Microwave Energy, Püschner MikrowellenEnergietechnik, pp. 1-4, Jun. 1997.
USP 30-NF25, Disintegration, pp. 276-277, 2007.
Matthes, R.; "Chapter 49" from website: http://www.ilo.org/safework_bookshelf/english?content&nd=857170571; made available online Oct. 12, 2004.
Google page showing the availability date of web reference U; provided Mar. 15, 2011.
Jones, P. L. et al, "Dielectric Drying", Drying Technology, 14(5), 1996, p. 1063-1098.
Guo, et al., Temperature and Moisture Dependent Dielectric Properties of Legume Flour Associated with Dielectric Heating, LWT Food Science and Technology 43, 2010, p. 193-201.
Katsuki, et al., Novel Energy-Saving Materials for Microwave Heating, Chem Mater. 2008, 20, p. 4803-4807.
Radio-Frequency Heating of Plastics, TechCommentary, vol. 4, No. 2, 1987, p. 1-4.
Jones, P. L., High Frequency Dielectric Heating in Paper Making, Drying Technology, 4(2), 1986, p. 217-244.
What is R.F. Heat Sealing?, Dielectric Sealing Service, Inc., 2007, p. 1-6.
Broadband RF Survey Instruments, ETS-Lindgren Haladay EMF Measurement, 2002, p. 1-2.
Lamp IR Infrared Heaters: Infrared Lamps for Controlled Concentrated Heating, Research Inc., p. 1-20., Sep. 20, 2010.
Callebaut, Power Quality & Utilisation Guide, Section 7: Energy Efficiency, Mar. 2007, www.leonardo-energy.org, p. 1-9.
Shukla, et al., Mouth Dissolving Tablets I: An Overview of Formulation Technology, Sci Pharm 2009, 76: p. 309-326.
Lieberman, Herbert A. et al., "Pharmaceutical Dosage Forms—Tablets", vol. 2, $2^{nd}$ Ed. pp. 213-217; 327-329, Marcel Dekker, Inc., 1990, New York and Basel.
Lachman, Leon et al., "The Theory and Practice of Industrial Pharmacy", $3^{rd}$ Ed., Chapter 11, pp. 293-345,Lea & Febiger, 1986, Philadelphia.
McConville, J. et al., "Erosion characteristics of an erodible tablet incorporated in a time-delayed capsule device," Drug Development and Industrial Pharmacy, vol. 31, No. 1, 2005, pp. 79-89, XP008108019.
USP 23 (1995) 1216, Tablet Friability, p. 1981.
USP 24, 2000 Version, Acetaminophen, pp. 19-20 and Ibuprofen, p. 856 (1999).
USP 30—NF25, Disintegration, pp. 276-277, 2007.
USP 33—U.S. Pharmacopeia, General Chapter 701—Disintegration, 2008.

(56) References Cited

OTHER PUBLICATIONS

Orally Disintegrating Tablets, draft Food and Drug Administration Guidance, Apr. 2007.
Heng, Paul Wan Sia, Chem Pharm Bull, 47 (5) 633-638 (1999).
Koral, Tony, Radio Frequency Heating and Post-Baking, Biscuit World, Issue 4, vol. 7, Nov. 2004.
Dielectric Heating with Microwave Energy, Püschner MikrowellenEnergietechnik, pp. 1-4.
Amin, Avani F., Emerging Treands in the Development of Orally Disintegrating Tablet Technology, Pharmainfo.net, vol. 4, Issue 1, Jan. 26, 2006; pp. 1-30.
Heng, P., et al., Melt Processes for Oral Solid Dosage Forms, Encyclopedia of Pharmaceutical Technology, vol. 4, Jan. 2, 2007, pp. 2257-2261.
International Search Report mailed Nov. 7, 2013 for corresponding Application No. PCT/US2013/039040.
International Search Report mailed Aug. 20, 2031 for Application No. PCT/US2013/039045.
International Search Report mailed Aug. 21, 2013 for Application No. PCT/US2013/039061.
European Search Report mailed Aug. 1, 2013 for Application No. EP08798740.
International Search Report mailed Aug. 20, 2013 for corresponding Patent Application No. PCT/US2013/039045.
International Search Report mailed Aug. 21, 2013 for corresponding Patent Application No. PCT/US2013/039061.
International Search Report mailed Jun. 8, 2013 for corresponding Patent Application No. PCT/US2013/039047.
European Search Report mailed Aug. 1, 2013 for Application No. E{08798740.
Maltodextrin (Maltrin M580), Apr. 20, 2000, (PFormulate Excipients).

* cited by examiner

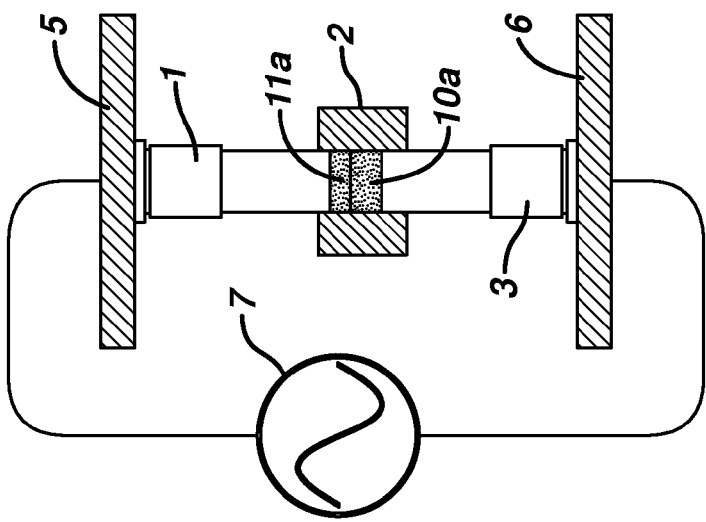
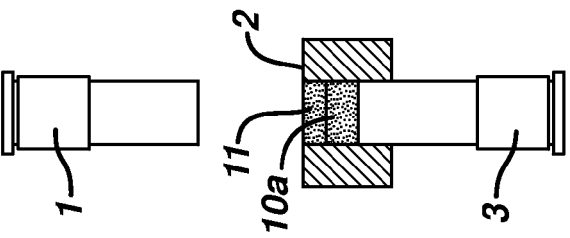
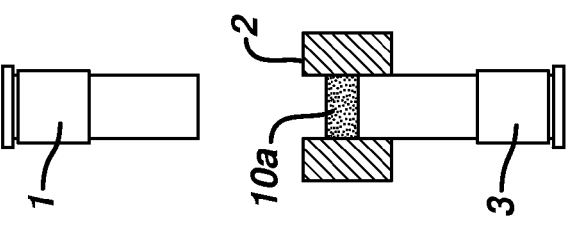
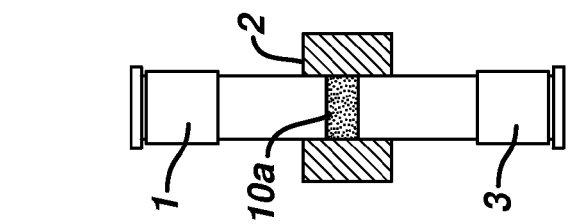
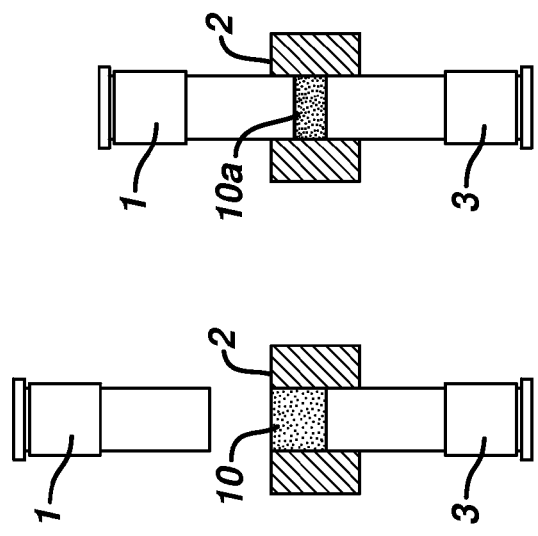

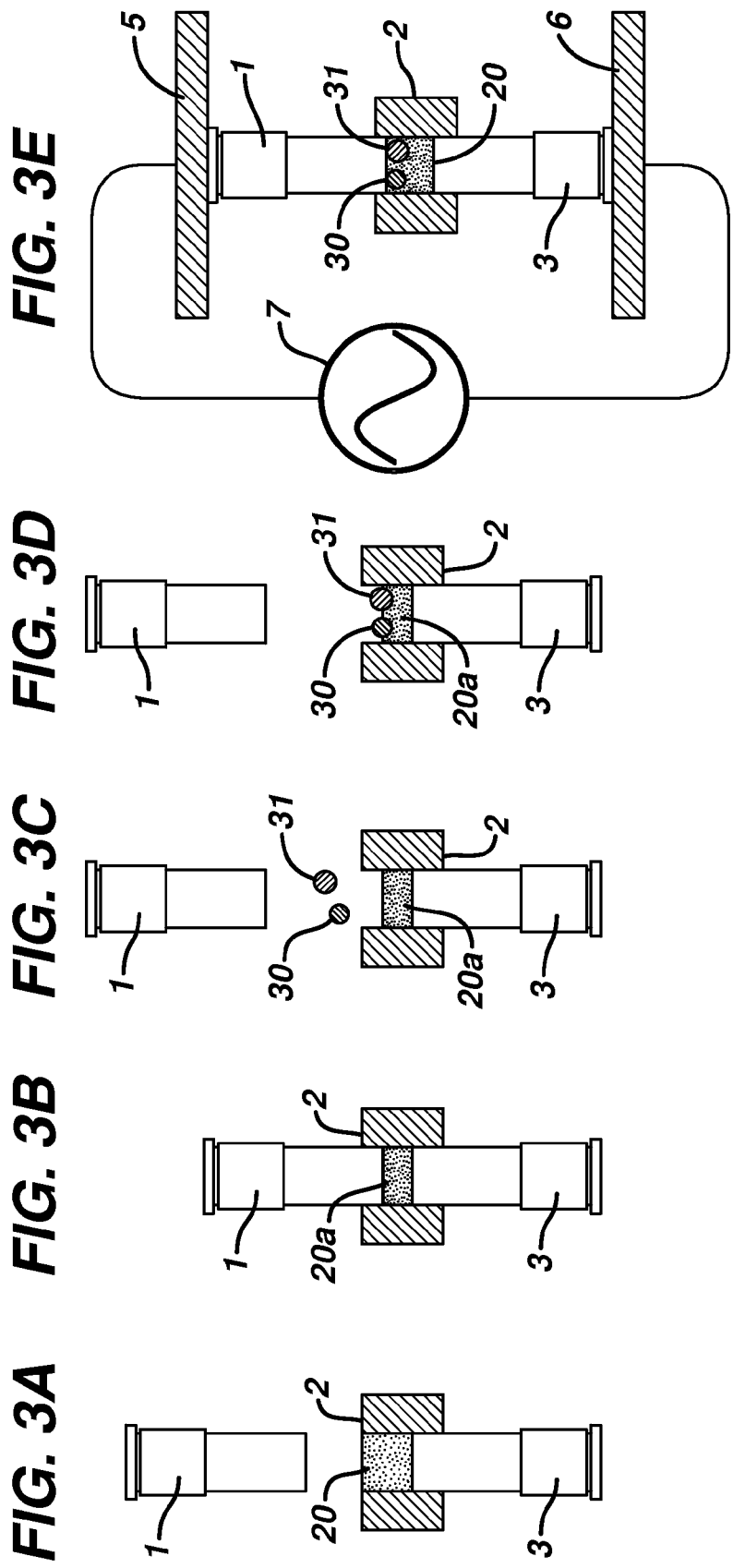

MACHINE FOR THE MANUFACTURE OF DOSAGE FORMS UTILIZING RADIOFREQUENCY ENERGY

CROSS REFERENCE TO RELATED APPLICATIONS

This application claims priority of the benefits of the filing of U.S. Provisional Application Ser. No. 61/245,315, filed Sep. 24, 2009, U.S. Provisional Application Ser. No. 61/255, 582, filed Oct. 28, 2009, U.S. Provisional Application Ser. No. 61/314,629, filed Mar. 17, 2010, and U.S. Provisional Application Ser. No. 61/358,167, filed Jun. 24, 2010. The complete disclosures of the aforementioned related U.S. patent applications are hereby incorporated herein by reference for all purposes.

BACKGROUND OF THE INVENTION

Pharmaceuticals intended for oral administration are typically provided in tablet form. Tablets are swallowed whole, chewed in the mouth, or disintegrated in the oral cavity. Soft tablets that either are chewed or dissolve in the mouth are often employed in the administration of pharmaceuticals where it is impractical to provide a tablet for swallowing whole. With chewable tablets, the act of chewing helps to break up the tablet particles as the tablet disintegrates and may increase the rate of absorption by the digestive tract. Soft tablets are also advantageous where it is desirable to make a pharmaceutically active agent available topically in the mouth or throat for both local effects and/or systemic absorption. Soft tablets are also utilized to improve drug administration in pediatric and geriatric patients. Soft tablets designed to disintegrate in the mouth prior to swallowing are particularly useful for improving compliance of pediatric patients.

Generally, soft tablets are made by compaction of a blend of powdered ingredients and typically include a pharmaceutically active agent, flavoring, and/or binders. The powder blend is typically fed into the cavity of a die of a tablet press and a tablet is formed by applying pressure. Hardness of the resulting tablet is a direct function of the compaction pressure employed and the compatibility of the ingredients in the formulation. A softer tablet, having an easier bite-through, may be prepared by employing reduced compaction pressures. The resulting tablet is softer, but also more fragile, brittle, and easily chipped and disadvantageously can involve complex and costly processing steps. Examples of soft tablets designed to disintegrate in the mouth without chewing are disclosed in U.S. Pat. Nos. 5,464,632, 5,223,264, 5,178,878, 6,589,554, and 6,224,905.

There is a need for aesthetically pleasing chewable and orally disintegrating tablets that utilizes compression-based tableting machines typically used to produce high density, hard swallowable tablets. When used at low compression forces, these machines typically produce highly friable tablets, which are not sufficiently stable during packaging, shipping, and storage. The present invention relates to the discovery of a machine and a process for making tablets, such as chewable or orally disintegrating tablets, using radiofrequency energy ("RF energy").

SUMMARY OF THE INVENTION

In one aspect, the present invention features a machine for the production of a solid dosage form (e.g., a tablet) including: (a) a die platen having one or more forming cavities each having an inner wall, a first opening at the surface of one side of the die platen, and a second opening at the surface on the opposite side of the die platen; (b) one or more first forming tools each adapted to move into one of the forming cavities through the first opening of the forming cavity; (c) one or more second forming tools each adapted to move adjacent to one of the second openings or into one of the forming cavities through the second opening of the forming cavity; (d) at least one first RF electrode operably associated with the one or more first forming tools, the one or more second forming tools, or the inner wall of the one or more forming cavities; and (e) at least one second RF electrode operably associated with the one or more first forming tools, the one or more second forming tools, or the inner wall of the one or more forming cavities; wherein the machine is adapted to form a dosage form between a first forming tool and a second forming tool within a forming cavity and wherein the first RF electrode and the second RF electrode are arranged within the machine such that when RF energy is conducted between the first RF electrode and the second RF electrode, the RF energy passes through the portion of the forming cavity adapted to form the dosage form. Examples of solid dosage forms include tablets (e.g., swallowable, chewable, and orally disintegrating tablets), gums, and lozenges.

The present invention also features a method of making a dosage form using such a machine by: (a) adding a powder blend to a forming cavity; (b) moving a first forming tool into the forming cavity through the first opening of the forming cavity such that the powder blend is formed into the shape of the dosage form within the forming cavity between the first forming tool and a second forming tool; (c) conducting RF energy between the first electrode and the second electrode such that the energy heats the powder blend within the forming cavity to form the dosage form; and (d) removing the dosage form from the forming cavity.

Other features and advantages of the present invention will be apparent from the detailed description of the invention and from the claims.

BRIEF DESCRIPTION OF THE FIGURES

FIGS. 2A-H are cross-section, side views of an embodiment of the invention showing the manufacture of a bilayer tablet 12 from powder blends 10 and 11 within die platen 2.

FIGS. 3A-G are cross-section, side views of an embodiment of the invention showing the manufacture of tablet 40 containing preformed inserts 30 and 31 from powder blend 20 within die platen 2.

FIG. 8 is a section view through the RF station rotary indexing machine 195 prior showing the manufacture of tablets 101a.

DETAILED DESCRIPTION OF THE INVENTION

Figure 1A:
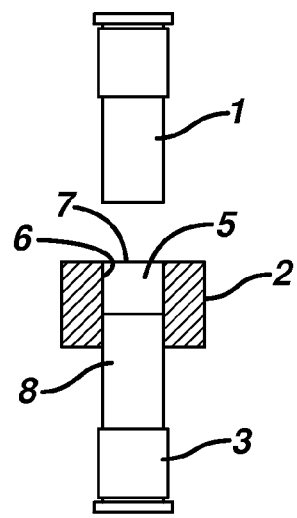
FIGS. 1A-F are cross-section, side views of an embodiment of the invention showing the manufacture of tablet 4a from powder blend 4 within die platen 2.

It is believed that one skilled in the art can, based upon the description herein, utilize the present invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

As discussed above, in one aspect, the present invention features a method of making a dosage form using such a machine by: (a) adding a powder blend to a forming cavity; (b) moving a first forming tool into the forming cavity through the first opening of the forming cavity such that the powder blend is formed into the shape of the dosage form within the forming cavity between the first forming tool and a second forming tool; (c) conducting RF energy between the first electrode and the second electrode such that the energy heats the powder blend within the forming cavity to form the dosage form; and (d) removing the dosage form from the forming cavity. While the specific embodiments herein focus on tablets, other dosage forms such as lozenges and chewing gums can also be made by such machine and process.

Powder Blend

As discussed above, the tablet is manufactured by compacting a powder blend containing a pharmaceutically active agent (as discussed herein), a meltable binder (as discussed herein), and optionally a pharmaceutically-acceptable carrier. The carrier contains one or more suitable excipients for the formulation of tablets. Examples of suitable excipients include, but are not limited to, fillers, adsorbents, disintegrants, lubricants, glidants, sweeteners, superdisintegrants, flavor and aroma agents, antioxidants, preservatives, texture enhancers, and mixtures thereof. One or more of the above ingredients may be present on the same particle of the powder blend.

Suitable fillers include, but are not limited to, carbohydrates (as discussed herein) and water insoluble plastically deforming materials (e.g., microcrystalline cellulose or other cellulosic derivatives), and mixtures thereof.

Suitable adsorbents include, but are not limited to, water-insoluble adsorbents such as dicalcium phosphate, tricalcium phosphate, silicified microcrystalline cellulose (e.g., such as distributed under the PROSOLV brand (PenWest Pharmaceuticals, Patterson, N.Y.)), magnesium aluminometasilicate (e.g., such as distributed under the NEUSILIN brand (Fuji Chemical Industries (USA) Inc., Robbinsville, N.J.)), clays, silicas, bentonite, zeolites, magnesium silicates, hydrotalcite, veegum, and mixtures thereof.

Suitable disintegrants include, but are not limited to, sodium starch glycolate, cross-linked polyvinylpyrrolidone, cross-linked carboxymethylcellulose, starches, microcrystalline cellulose, and mixtures thereof.

Suitable lubricants include, but are not limited to, long chain fatty acids and their salts, such as magnesium stearate and stearic acid, talc, glycerides waxes, and mixtures thereof.

Suitable glidants include, but are not limited to, colloidal silicon dioxide.

Examples of sweeteners include, but are not limited to, synthetic or natural sugars; artificial sweeteners such as saccharin, sodium saccharin, aspartame, acesulfame, thaumatin, glycyrrhizin, sucralose, dihydrochalcone, alitame, miraculin, monellin, and stevside; sugar alcohols such as sorbitol, mannitol, glycerol, lactitol, maltitol, and xylitol; sugars extracted from sugar cane and sugar beet (sucrose), dextrose (also called glucose), fructose (also called laevulose), and lactose (also called milk sugar); isomalt, salts thereof, and mixtures thereof.

Examples of superdisintegrants include, but are not limited to, croscarmellose sodium, sodium starch glycolate and cross-linked povidone (crospovidone). In one embodiment the tablet contains up to about 5% by weight of such superdisintegrant.

Examples of flavors and aromatics include, but are not limited to, essential oils including distillations, solvent extractions, or cold expressions of chopped flowers, leaves, peel or pulped whole fruit containing mixtures of alcohols, esters, aldehydes and lactones; essences including either diluted solutions of essential oils, or mixtures of synthetic chemicals blended to match the natural flavor of the fruit (e.g., strawberry, raspberry and black currant); artificial and natural flavors of brews and liquors, e.g., cognac, whisky, rum, gin, sherry, port, and wine; tobacco, coffee, tea, cocoa, and mint; fruit juices including expelled juice from washed, scrubbed fruits such as lemon, orange, and lime; spear mint, pepper mint, wintergreen, cinnamon, cacoe/cocoa, vanilla, liquorice, menthol, eucalyptus, aniseeds nuts (e.g., peanuts, coconuts, hazelnuts, chestnuts, walnuts, colanuts), almonds, raisins; and powder, flour, or vegetable material parts including tobacco plant parts, e.g., genus Nicotiana, in amounts not contributing significantly to the level of nicotine, and ginger.

Examples of antioxidants include, but are not limited to, tocopherols, ascorbic acid, sodium pyrosulfite, butylhydroxytoluene, butylated hydroxyanisole, edetic acid, and edetate salts, and mixtures thereof.

Examples of preservatives include, but are not limited to, citric acid, tartaric acid, lactic acid, malic acid, acetic acid, benzoic acid, and sorbic acid, and mixtures thereof.

Examples of texture enhancers include, but are not limited to, pectin, polyethylene oxide, and carrageenan, and mixtures thereof. In one embodiment, texture enhancers are used at levels of from about 0.1% to about 10% percent by weight.

In one embodiment of the invention, the powder blend has an average particle size of less than 500 microns, such as from about 50 microns to about 500 microns, such as from about 50 microns and 300 microns. Particles in this size range are particularly useful for direct compacting processes.

In one embodiment of the invention, the tablet may be a made from a powder blend that is substantially free of hydrated polymers. As used herein, what is meant by "substantially free" is less than 5%, such as less than 1%, such as less than 0.1%, such as completely free (e.g., 0%). Such a composition is advantageous for maintaining an immediate release dissolution profile, minimizing processing and material costs, and providing for optimal physical and chemical stability of the tablet.

In one embodiment, powder blend/tablet is substantially free of directly compressible water insoluble fillers. Water insoluble fillers include but are not limited to microcrystalline cellulose, directly compressible microcrystalline cellulose, celluloses, water insoluble celluloses, starch, cornstarch and modified starches. As described in this embodiment, substantially free is less than 2 percent, e.g. less than 1 percent or none.

Meltable Binder

The powder blend/tablet of the present invention includes at least one meltable binder. In one embodiment, the meltable binder has a melting point of from about 40° C. to about 140° C., such as from about 55° C. to about 100° C. The softening or melting of the meltable binder(s) results in the sintering of the tablet shape through the binding of the softened or melted binder with the pharmaceutically active agent and/or other ingredients within the compacted powder blend.

In one embodiment, the meltable binder is a RF-meltable binder. What is meant by an RF-meltable binder is a solid binder that can be softened or melted upon exposure to RF energy. The RF-meltable binder typically is polar and has the capability to re-harden or resolidify upon cooling.

In one embodiment, the meltable binder is not a RF-meltable binder. In such embodiment, the powder blend contains an excipient that heats upon exposure to RF energy (e.g., a polar excipient), such that the resulting heat from is able to soften or melt the meltable binder. Examples of such excipients include, but are not limited to, polar liquids such as water and glycerin; powdered metals and metal salts such as powdered iron, sodium chloride, aluminum hydroxide, and magnesium hydroxide; stearic acid; and sodium stearate.

Examples of suitable meltable binders include: fats such as cocoa butter, hydrogenated vegetable oil such as palm kernel oil, cottonseed oil, sunflower oil, and soybean oil; mono, di, and triglycerides; phospholipids; cetyl alcohol; waxes such as Carnauba wax, spermaceti wax, beeswax, candelilla wax, shellac wax, microcrystalline wax, and paraffin wax; water soluble polymers such as polyethylene glycol, polycaprolactone, GlycoWax-932, lauroyl macrogol-32 glycerides, and stearoyl macrogol-32 glycerides; polyethylene oxides; and sucrose esters.

In one embodiment, the meltable binder is a RF-meltable binder, and the RF-meltable binder is a polyethylene glycol (PEG), such as PEG-4000. A particularly preferred RF-meltable binder is PEG having at least 95% by weight of the PEG particles less than 100 microns (as measured by conventional means such as light or laser scattering or sieve analysis) and a molecular weight between 3000 and 8000 Daltons.

The meltable binder(s) may be present at level of about 0.01 percent to about 70 percent of the powder blend/tablet, such as from about 1 percent to about 50 percent, such as from about 10 percent to about 30 percent of the powder blend/tablet.

Carbohydrate

In one embodiment, the powder blend contains at least one carbohydrate. The carbohydrate can contribute to the dissolvability and mouth feel of the tablet, aid in distributing the meltable binder across a broader surface area, and diluting and cushioning the pharmaceutically active agent. Examples of carbohydrates include, but are not limited to, water-soluble compressible carbohydrates such as sugars (e.g., dextrose, sucrose, maltose, isomalt, and lactose), starches (e.g., corn starch), sugar-alcohols (e.g., mannitol, sorbitol, maltitol, erythritol, lactitol, and xylitol), and starch hydrolysates (e.g., dextrins, and maltodextrins).

The carbohydrate(s) may be present at level of about 5 percent to about 95 percent of the powder blend/tablet, such as from about 20 percent to about 90 percent or from about 40 percent to about 80 percent of the powder blend/tablet. The particle size of the of carbohydrate can influence the level of meltable binder used, wherein a higher particle size of carbohydrate provides a lower surface area and subsequently requires a lower level of meltable binder. In one embodiment, wherein the carbohydrate(s) is greater than 50% by weight of the powder blend and the mean particle size of the carbohydrate(s) is greater than 100 microns, then the meltable binder is from about 10 to about 30 percent by weight of the powder blend/tablet.

Pharmaceutically Active Agent

The powder blend/tablet of the present invention includes at least one pharmaceutically active agent. What is meant by a "pharmaceutically active agent" is an agent (e.g., a compound) that is permitted or approved by the U.S. Food and Drug Administration, European Medicines Agency, or any successor entity thereof, for the oral treatment of a condition or disease. Suitable pharmaceutically active agents include, but are not limited to, analgesics, anti-inflammatory agents, antipyretics, antihistamines, antibiotics (e.g., antibacterial, antiviral, and antifungal agents), antidepressants, antidiabetic agents, antispasmodics, appetite suppressants, bronchodilators, cardiovascular treating agents (e.g., statins), central nervous system treating agents, cough suppressants, decongestants, diuretics, expectorants, gastrointestinal treating agents, anesthetics, mucolytics, muscle relaxants, osteoporosis treating agents, stimulants, nicotine, and sedatives.

Examples of suitable gastrointestinal treating agents include, but are not limited to: antacids such as aluminum-containing pharmaceutically active agents (e.g., aluminum carbonate, aluminum hydroxide, dihydroxyaluminum sodium carbonate, and aluminum phosphate), bicarbonate-containing pharmaceutically active agents, bismuth-containing pharmaceutically active agents (e.g., bismuth aluminate, bismuth carbonate, bismuth subcarbonate, bismuth subgallate, and bismuth subnitrate), calcium-containing pharmaceutically active agents (e.g., calcium carbonate), glycine, magnesium-containing pharmaceutically active agents (e.g., magaldrate, magnesium aluminosilicates, magnesium carbonate, magnesium glycinate, magnesium hydroxide, magnesium oxide, and magnesium trisilicate), phosphate-containing pharmaceutically active agents (e.g., aluminum phosphate and calcium phosphate), potassium-containing pharmaceutically active agents (e.g., potassium bicarbonate), sodium-containing pharmaceutically active agents (e.g., sodium bicarbonate), and silicates; laxatives such as stool softeners (e.g., docusate) and stimulant laxatives (e.g., bisacodyl); H2 receptor antagonists, such as famotidine, ranitidine, cimetadine, and nizatidine; proton pump inhibitors such as omeprazole, dextansoprazole, esomeprazole, pantoprazole, rabeprazole, and lansoprazole; gastrointestinal cytoprotectives, such as sucraflate and misoprostol; gastrointestinal prokinetics such as prucalopride; antibiotics for *H. pylori*, such as clarithromycin, amoxicillin, tetracycline, and metronidazole; antidiarrheals, such as bismuth subsalicylate, kaolin, diphenoxylate, and loperamide; glycopyrrolate; analgesics, such as mesalamine; antiemetics such as ondansetron, cyclizine, diphenyhydroamine, dimenhydrinate, meclizine, promethazine, and hydroxyzine; probiotic bacteria including but not limited to lactobacilli; lactase; racecadotril; and anti-flatulents such as polydimethylsiloxanes (e.g., dimethicone and simethicone, including those disclosed in U.S. Pat. Nos. 4,906,478, 5,275,822, and 6,103,260); isomers thereof; and pharmaceutically acceptable salts and prodrugs (e.g., esters) thereof.

Examples of suitable analgesics, anti-inflammatories, and antipyretics include, but are not limited to, non-steroidal anti-inflammatory drugs (NSAIDs) such as propionic acid derivatives (e.g., ibuprofen, naproxen, ketoprofen, flurbiprofen, fenbufen, fenoprofen, indoprofen, ketoprofen, fluprofen, pirprofen, carprofen, oxaprozin, pranoprofen, and suprofen) and COX inhibitors such as celecoxib; acetaminophen; acetyl salicylic acid; acetic acid derivatives such as indomethacin, diclofenac, sulindac, and tolmetin; fenamic acid derivatives such as mefanamic acid, meclofenamic acid, and flufenamic acid; biphenylcarbodylic acid derivatives such as diflunisal and flufenisal; and oxicams such as piroxicam, sudoxicam, isoxicam, and meloxicam; isomers thereof; and pharmaceutically acceptable salts and prodrugs thereof.

Examples of antihistamines and decongestants, include, but are not limited to, bromopheniramine, chlorcyclizine, dexbrompheniramine, bromhexane, phenindamine, pheniramine, pyrilamine, thonzylamine, pripolidine, ephedrine, phenylephrine, pseudoephedrine, phenylpropanolamine, chlorpheniramine, dextromethorphan, diphenhydramine, doxylamine, astemizole, terfenadine, fexofenadine, naphazoline, oxymetazoline, montelukast, propylhexadrine, triprolidine, clemastine, acrivastine, promethazine, oxomemazine, mequitazine, buclizine, bromhexine, ketotifen, terfenadine, ebastine, oxatamide, xylomeazoline, loratadine, desloratadine, and cetirizine; isomers thereof; and pharmaceutically acceptable salts and esters thereof.

Examples of cough suppressants and expectorants include, but are not limited to, diphenhydramine, dextromethorphan, noscapine, clophedianol, menthol, benzonatate, ethylmorphone, codeine, acetylcysteine, carbocisteine, ambroxol, belladona alkaloids, sobrenol, guaiacol, and guaifenesin; isomers thereof; and pharmaceutically acceptable salts and prodrugs thereof.

Examples of muscle relaxants include, but are not limited to, cyclobenzaprine and chlorzoxazone metaxalone, orphenadrine, and methocarbamol; isomers thereof; and pharmaceutically acceptable salts and prodrugs thereof.

Examples of stimulants include, but are not limited to, caffeine.

Examples of sedatives include, but are not limited to sleep aids such as antihistamines (e.g., diphenhydramine), eszopiclone, and zolpidem, and pharmaceutically acceptable salts and prodrugs thereof.

Examples of appetite suppressants include, but are not limited to, phenylpropanolamine, phentermine, and diethylcathinone, and pharmaceutically acceptable salts and prodrugs thereof Examples of anesthetics (e.g., for the treatment of sore throat) include, but are not limited to dyclonine, benzocaine, and pectin and pharmaceutically acceptable salts and prodrugs thereof.

Examples of suitable statins include but are not limited to atorvastin, rosuvastatin, fluvastatin, lovastatin, simvustatin, atorvastatin, pravastatin and pharmaceutically acceptable salts and prodrugs thereof.

In one embodiment, the pharmaceutically active agent included within the tablet is selected from phenylephrine, dextromethorphan, pseudoephedrine, acetaminophen, cetirizine, aspirin, nicotine, ranitidine, ibuprofen, ketoprofen, loperamide, famotidine, calcium carbonate, simethicone, chlorpheniramine, methocarbomal, chlophedianol, ascorbic acid, pectin, dyclonine, benzocaine and menthol, and pharmaceutically acceptable salts and prodrugs thereof.

As discussed above, the pharmaceutically active agents of the present invention may also be present in the form of pharmaceutically acceptable salts, such as acidic/anionic or basic/cationic salts. Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Pharmaceutically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc.

As discussed above, the pharmaceutically active agents of the present invention may also be present in the form of prodrugs of the pharmaceutically active agents. In general, such prodrugs will be functional derivatives of the pharmaceutically active agent, which are readily convertible in vivo into the required pharmaceutically active agent. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Where the pharmaceutically active agents according to this invention have at least one chiral center, they may accordingly exist as enantiomers. Where the pharmaceutically active agents possess two or more chiral centers, they may additionally exist as diastereomers. It is to be understood that all such isomers and mixtures thereof are encompassed within the scope of the present invention. Furthermore, some of the crystalline forms for the pharmaceutically active agents may exist as polymorphs and as such are intended to be included in the present invention. In addition, some of the pharmaceutically active agents may form solvates with water (e.g., hydrates) or common organic solvents, and such solvates are also intended to be encompassed within the scope of this invention.

In one embodiment, the pharmaceutically active agent or agents are present in the tablet in a therapeutically effective amount, which is an amount that produces the desired therapeutic response upon oral administration and can be readily determined by one skilled in the art. In determining such amounts, the particular pharmaceutically active agent being administered, the bioavailability characteristics of the pharmaceutically active agent, the dose regime, the age and weight of the patient, and other factors must be considered, as known in the art.

The pharmaceutically active agent may be present in various forms. For example, the pharmaceutically active agent may be dispersed at the molecular level, e.g. melted, within the tablet, or may be in the form of particles, which in turn may be coated or uncoated. If the pharmaceutically active agent is in form of particles, the particles (whether coated or uncoated) typically have an average particle size of from about 1 to about 2000 microns. In one embodiment, such particles are crystals having an average particle size of from about 1 to about 300 microns. In another embodiment, the particles are granules or pellets having an average particle size of from about 50 to about 2000 microns, such as from about 50 to about 1000 microns, such as from about 100 to about 800 microns.

The pharmaceutically active agent may be present in pure crystal form or in a granulated form prior to the addition of the taste masking coating. Granulation techniques may be used to improve the flow characteristics or particle size of the pharmaceutically active agents to make it more suitable for compaction or subsequent coating. Suitable binders for making the granulation include but are not limited to starch, polyvinylpyrrolidone, polymethacrylates, hydroxypropylmethylcellulose, and hydroxypropylcellulose. The particles including pharmaceutically active agent(s) may be made by cogranulating the pharmaceutically active agent(s) with suitable substrate particles via any of the granulation methods known in the art. Examples of such granulation method include, but are not limited to, high sheer wet granulation and fluid bed granulation such as rotary fluid bed granulation.

If the pharmaceutically active agent has an objectionable taste, the pharmaceutically active agent may be coated with a taste masking coating, as known in the art. Examples of suitable taste masking coatings are described in U.S. Pat. No. 4,851,226, U.S. Pat. No. 5,075,114, and U.S. Pat. No. 5,489,436. Commercially available taste masked pharmaceutically active agents may also be employed. For example, acetaminophen particles, which are encapsulated with ethylcellulose or other polymers by a coacervation process, may be used in the present invention. Coacervation-encapsulated acetaminophen may be purchased commercially from Eurand America, Inc. (Vandalia, Ohio) or from Circa Inc. (Dayton, Ohio).

In one embodiment, the tablet incorporates modified release coated particles (e.g., particles containing at least one pharmaceutically active agent that convey modified release properties of such agent). As used herein, "modified release" shall apply to the altered release or dissolution of the active agent in a dissolution medium, such as gastrointestinal fluids. Types of modified release include, but are not limited to, sustained release or delayed release. In general, modified release tablets are formulated to make the active agents(s) available over an extended period of time after ingestion, which thereby allows for a reduction in dosing frequency compared to the dosing of the same active agent(s) in a conventional tablet. Modified release tablets also permit the use of active agent combinations wherein the duration of one pharmaceutically active agent may differ from the duration of another pharmaceutically active agent. In one embodiment the tablet contains one pharmaceutically active agent that is released in an immediate release manner and an additional active agent or a second portion of the same active agent as the first that is modified release.

Examples of swellable, erodible hydrophilic materials for use as a release modifying excipient for use in the modified release coating include water swellable cellulose derivatives, polyalkylene glycols, thermoplastic polyalkylene oxides, acrylic polymers, hydrocolloids, clays, and gelling starches. Examples of water swellable cellulose derivatives include sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose. Examples of polyalkylene glycols include polyethylene glycol. Examples of suitable thermoplastic polyalkylene oxides include poly (ethylene oxide). Examples of acrylic polymers include potassium methacrylatedivinylbenzene copolymer, polymethylmethacrylate, and high-molecular weight cross-linked acrylic acid homopolymers and copolymers.

Suitable pH-dependent polymers for use as release-modifying excipients for use in the modified release coating include: enteric cellulose derivatives such as hydroxypropyl methylcellulose phthalate, hydroxypropyl methylcellulose acetate succinate, and cellulose acetate phthalate; natural resins such as shellac and zein; enteric acetate derivatives such as polyvinylacetate phthalate, cellulose acetate phthalate, and acetaldehyde dimethylcellulose acetate; and enteric acrylate derivatives such as for example polymethacrylate-based polymers such as poly(methacrylic acid, methyl methacrylate) 1:2 (available from Rohm Pharma GmbH under the tradename EUDRAGIT S) and poly(methacrylic acid, methyl methacrylate) 1:1 (available from Rohm Pharma GmbH under the tradename EUDRAGIT L).

In one embodiment the pharmaceutically active agent is coated with a combination of a water insoluble film forming polymer (such as but not limited to cellulose acetate or ethylcellulose) and a water soluble polymer (such as but not limited to povidone, polymethacrylic co-polymers such as those sold under the tradename Eudragit E-100 from Rohm America, and hydroxypropylcellulose). In this embodiment, the ratio of water insoluble film forming polymer to water soluble polymer is from about 50 to about 95 percent of water insoluble polymer and from about 5 to about 50 percent of water soluble polymer, and the weight percent of the coating by weight of the coated taste-masked particle is from about 5 percent to about 40 percent. In one embodiment, the coating which is used in the coated particle of the pharmaceutically active agent is substantially free of a material (such as polyethylene glycol) which melts below 85° C., in order to prevent damage to the integrity of the coating during the RF heating step.

In one embodiment, one or more pharmaceutically active agents or a portion of the pharmaceutically active agent may be bound to an ion exchange resin for the purposes of taste-masking the pharmaceutically active agent or delivering the active in a modified release manner.

In one embodiment, the pharmaceutically active agent is capable of dissolution upon contact with a fluid such as water, stomach acid, intestinal fluid or the like. In one embodiment, the dissolution characteristics of the pharmaceutically active agent within the tablet meets USP specifications for immediate release tablets including the pharmaceutically active agent. For example, for acetaminophen tablets, USP 24 specifies that in pH 5.8 phosphate buffer, using USP apparatus 2 (paddles) at 50 rpm, at least 80% of the acetaminophen contained in the tablet is released there from within 30 minutes after dosing, and for ibuprofen tablets, USP 24 specifies that in pH 7.2 phosphate buffer, using USP apparatus 2 (paddles) at 50 rpm, at least 80% of the ibuprofen contained in the tablet is released there from within 60 minutes after dosing. See USP 24, 2000 Version, 19-20 and 856 (1999). In another embodiment, the dissolution characteristics of the pharmaceutically active agent are modified: e.g. controlled, sustained, extended, retarded, prolonged, delayed and the like.

In one embodiment, the particle size of the pharmaceutically active agent causes more void spaces to be present in the tablet, wherein a higher particle size of the pharmaceutically active agent subsequently requires a lower level of meltable binder. In one embodiment, wherein the pharmaceutically active agent or coated pharmaceutically active agent(s) is greater than 50% of the blend by weight of the powder blend/tablet and the mean particle size of the carbohydrate is greater than 100 microns, the meltable binder is from about 10 to about 30 percent by weight of the powder blend/tablet. In one embodiment, wherein the mean particle size of the powder blend is between about 100 microns and about 300 microns, then meltable binder is from about 10 to about 20 percent by weight of the powder blend/tablet.

The melting point of the pharmaceutically active agent can have an impact on the temperature used during the heating step and the type of meltable binder used. In one embodiment, the melting point of the meltable binder is less than the melting point of the pharmaceutically active agent. In another embodiment, the melting point of the pharmaceutically active agent is the same or lower than the melting point of the meltable binder, in which case during the fusing or heating step, both the pharmaceutically active agent and the meltable binder may melt and create a eutectic or various bridges of the pharmaceutically active agent and meltable binder between the other materials in the tablet form upon cooling. In one embodiment, the heating temperature is above the melting point of the meltable binder and below the melting point of the pharmaceutically active agent. In one embodiment wherein ibuprofen is the pharmaceutically active agent, the meltable binder is heated from about 30° C. to about 60° C. In one embodiment, the pharmaceutically active agent is the meltable binder.

In one embodiment, the pharmaceutically active agent is in the form of a particle that is coated with the meltable binder.

The susceptibility to RF energy of the pharmaceutically active agent (e.g., to melt or degrade) can have an impact on the type of energy and/or temperature used during the heating step as well as the type of the meltable binder used.

In one embodiment, the processing of the tablet is free of a wet or hot melt granulation step. In this embodiment, the materials are directly blended prior to the addition of heat. In one embodiment, the materials are directly blended and compressed prior to the addition of heat.

Manufacture of Tablet Shape

In one embodiment, the powder blend is fed into the tablet die of an apparatus that applies pressure to form the tablet shape (e.g., by light compaction such as tamping). Any suitable compacting apparatus may be used, including, but not limited to, a conventional unitary or rotary tablet press. In one embodiment, the tablet shape may be formed by compaction using a rotary tablet press (e.g., such as those commercially available from Fette America Inc., Rockaway, N.J. or Manesty Machines LTD, Liverpool, UK). In one embodiment, the tablet shape is heated after it is removed from the tablet press. In another embodiment, the tablet shape is heated within the tablet press.

In one embodiment, to obtain desired attribute of an orally disintegrating tablet, the tablet's construction may be highly porous, use a minimal amount of binder, and/or have a low density. Such tablets, therefore, are somewhat fragile and soft. In a preferred embodiment, a minimum of tamping/compaction force is desired to achieve the orally disintegrating property (low density). Experiments have determined that low force compaction without application of RF energy produced very fragile tablets that could not withstand the forces of material handling required in manufacturing. It was also determined that when a compacted tablet described above is carefully handled and brought to a heat source (RF or conventional convection/conduction) the tablet "slumps" and deforms under its own weight as the binders become molten.

In most thermodynamic processes or machines, the heat source and the heat sink are two distinct machines or steps requiring material to be transferred from one apparatus to the other. In the manufacture of the tablets of the present invention, the energy must be added to the tablet to achieve the binding effect and then must be removed from the product to solidify and strengthen it for its final handling packaging and use. One of the unique and unanticipated attributes of one embodiment of the manufacturing process of the present invention is that heat source and heat sink are part of the same apparatus. In fact in early experiments the metallic forming tool (e.g., a die punch) which was at room temperature removed so much heat from the treated tablet shape (due to its high thermal conductivity) that the surface of the resulting tablet was unacceptable due to the fact that uniform melting within the powder blend had not taken place. The resulting tablet had a well formed core, but the surface was loose unbound and poorly formed powder that did not adhere to the rest of the tablet. To correct for this thermal loss, in one embodiment, heat is added to the forming tools to achieve proper sintering at the surface as well as at the center of the tablet.

To exploit this unique thermal effect, powder blends can also be chosen for their thermal properties and thermal conductivity and specific heat such that the powder blend particles themselves become heat sinks. In a typical orally disintegrating tablet ("ODT") formulation the polar binders that heat in the RF field may compose less than 10% of the mixture. The remaining 90% of the materials act as a heat sink that quickly removes heat from the binders once the RF field is removed. The desirable result of this is that the total process time can be just a few seconds and that the tablet does not need to be transferred from the die platen during the critical tamping and heating process. The die platen can function then as a material handling apparatus as well as a thermal forming tool. This is particularly advantageous for successful manufacture of fragile orally disintegrating tablets.

In one embodiment, the compaction step (e.g., tamping) which occurs prior to the addition of the RF energy utilizes a compaction force which is less than the force required to compress a chewable or swallowable tablet. In one embodiment, the compaction force is less than about 1000 pounds per square inch (e.g., less than about 500 pounds per square inch, such as less than 200 pounds per square inch, such as less than 50 pounds per square inch). In one embodiment, the energy is applied while the powder blend is under such force.

In one embodiment, the compaction step occurs in an indexed manner, where one set of tablets are compacted simultaneously, before rotating to another indexing station. In one embodiment, the compaction step occurs at a single indexing station and the application of RF energy occurs at a separate indexing station. In another embodiment, a third indexing station is present wherein the ejection of the tablet or multiple tablets occurs, wherein the lower forming tool is raised up through and up to the surface of the die. In another embodiment the compaction step is performed through the addition of air pressure or hydraulic cylinder to the top of the upper forming tools. In one embodiment multiple tablets are ejected simultaneously and separated from the surface of the indexing station and removed via a take-off bar.

In another embodiment, the tablet shape may be prepared by the compaction methods and apparatus described in United States Patent Application Publication No. 20040156902. Specifically, the tablet shape may be made using a rotary compression module including a fill zone, insertion zone, compression zone, ejection zone, and purge zone in a single apparatus having a double row die construction. The dies of the compression module may then be filled using the assistance of a vacuum, with filters located in or near each die. The purge zone of the compression module includes an optional powder blend recovery system to recover excess powder blend from the filters and return the powder blend to the dies. In one embodiment the RF energy source is projected through the die table of a rotary press into the appropriate electrode within the forming tool or the forming cavity. In one embodiment the die table is constructed of non-conductive material.

In another embodiment, a portion of the tablet shape may be prepared by a wet-granulation method, in which the excipients and a solution or dispersion of a wet binder (e.g., an aqueous cooked starch paste or solution of polyvinyl pyrrolidone) are mixed and granulated. Suitable apparatus for wet granulation include low shear mixers (e.g., planetary mixers), high shear mixers, and fluid beds (including rotary fluid beds). The resulting granulated material may then be dried, and optionally dry-blended with further ingredients (e.g., excipients such as, for example, the meltable binder described in the invention herein, lubricants, colorants, and the like). The final dry blend is then suitable for compaction by the methods described herein. Methods for direct compaction and wet granulation processes are known in the art.

In one embodiment, the tablet shape is prepared by the compaction methods and apparatus described in issued U.S. Pat. No. 6,767,200. Specifically, the tablet shape is made using a rotary compression module including a fill zone, compression zone, and ejection zone in a single apparatus having a double row die construction as shown in FIG. 6 therein. The dies of the compression module are preferably filled using the assistance of a vacuum, with filters located in or near each die.

The tablet shape may have one of a variety of different shapes. For example, the tablet shape may be shaped as a polyhedron, such as a cube, pyramid, prism, or the like; or may have the geometry of a space figure with some non-flat faces, such as a cone, truncated cone, triangle, cylinder, sphere, torus, or the like. In certain embodiments, a tablet shape has one or more major faces. For example, the tablet shape surface typically has opposing upper and lower faces formed by contact with the upper and lower forming tool faces (e.g., die punches) in the compaction machine. In such embodiments, the tablet shape surface typically further includes a "belly-band" located between the upper and lower faces, and formed by contact with the die walls in the compaction machine. A tablet shape/tablet may also be a multi-layer. Applicants have found that sharp edges in the tooling used to make the tablets can cause arcing, and thus more rounded edges may be needed.

In one embodiment, the method of producing the tablet shape is substantially free of the use of solvents. In this embodiment, the powder blend is substantially free of solvents, and the manufacturing process (e.g., filling process into the die) is also substantially free of solvents. Solvents may include, but are not limited to, water, organic solvents such as but not limited to alcohols, chlorinated solvents, hexanes, or acetone; or gaseous solvents such as but not limited to nitrogen, carbon dioxide or supercritical fluids.

In one embodiment a vibratory step is utilized (e.g., added after filling of the powder blend but prior to the heating or fusing step, in order to remove air from the powder blend). In one embodiment a vibration with the frequency from about 1 Hz to about 50 KHz is added with amplitude from 1 micron to 5 mm peak-to-peak to allow for the flowable powder blend to settle into the cavity of a the die platen ("forming cavity").

Figure 1B:
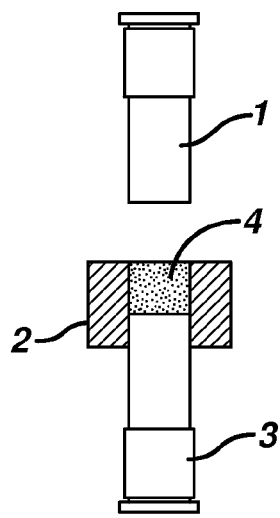
Figure 1C:
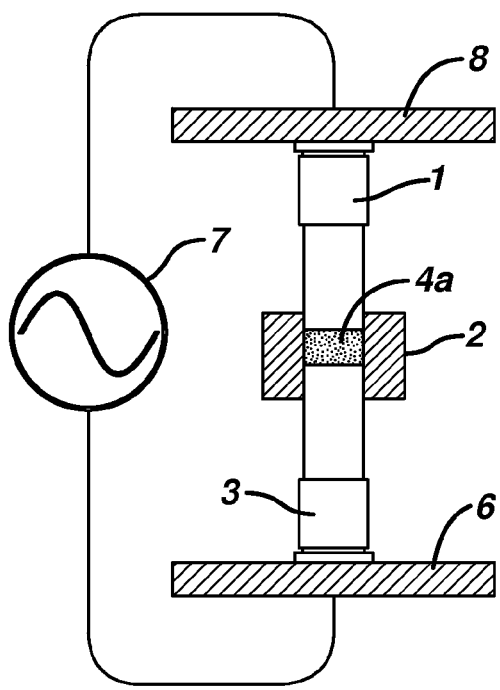

In one embodiment, as shown in FIGS. 1A-1F, a metered volume of powder blend 4 is filled into a Teflon® (or similar electrical and RF energy insulative material such as ceramic or UHMW plastic) die platen 2. Die platen 2 has forming cavity 5 with inner wall 6, upper opening 7 on the upper surface of die platen 2 (which allows powder blend 4 and upper forming tool 1 to move into the forming cavity 5), and lower opening 8 on the opposite surface of die platen 2 (which allows powder blend 4 and lower forming tool 3 to move into the forming cavity 5). Powder blend 4 may be either gravity fed or mechanically fed from a feeder (not shown). A metallic, electrically conductive lower forming tool 3 is inserted into the die platen to retain the powder blend 4, within die platen 2. A similar metallic, electrically conductive upper forming tool 1 is positioned above the die platen 2 as shown in FIG. 1B. The forming tools 1 and 3, die platen 2, and powder blend 4 are then moved to a compaction and RF heating station as shown in FIG. 1C to form tablet shape 4a.

Figure 1D:
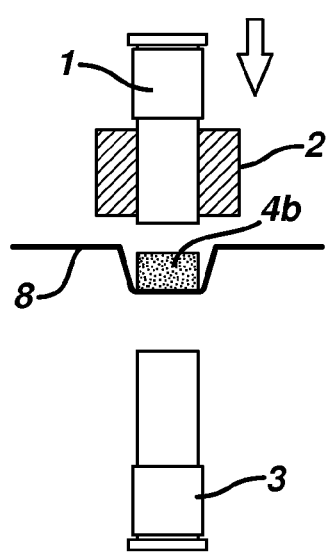
Figure 1E:
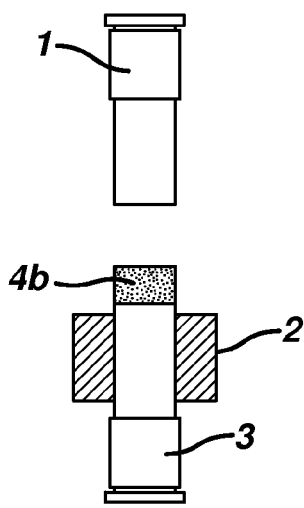
Figure 1F:
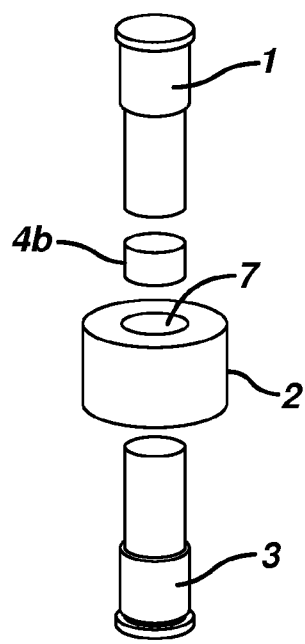

This heating station is comprised of an RF generator 7 which produces the necessary high voltage, high frequency energy. The generator 7 is electrically connected to movable upper RF electrode plate 8 and movable lower RF electrode plate 6. As shown in FIG. 1C, at this position, the powder blend 4 is compacted between an upper forming tool 1 and a lower forming tool 3 by pressure exerted by upper RF electrode plate 8 and lower electrode plate 6 to form tablet shape 4a. Tablet shape 4a is then exposed to RF energy from RF generator 7, which heats the meltable binder within tablet shape 4a. After the RF energy is switched off, tablet shape 4a cools to form the tablet 4b. In one embodiment, as shown in FIG. 1D, tablet 4b is pushed by upper forming tool 1 from the die platen 2 into blister 8, which is used to package tablet 4b. In an alternative embodiment, as shown in FIG. 1E, tablet 4b is pushed from the die platen 2 by the lower forming tool 3 and guided to an ejection chute by a stationary "take-off" bar (not shown). FIG. 1F shows a 3 dimensional representation of the forming tools 1 and 4, die platen 2, and tablet 4b.

Figure 2F:
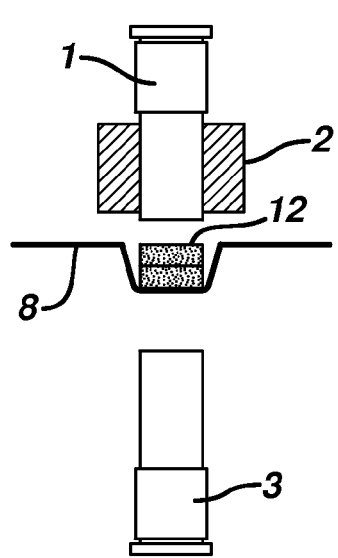
Figure 2G:
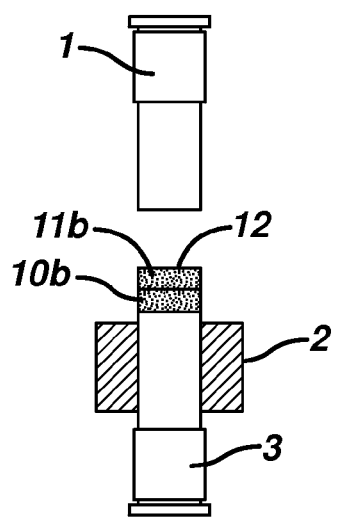
Figure 2H:
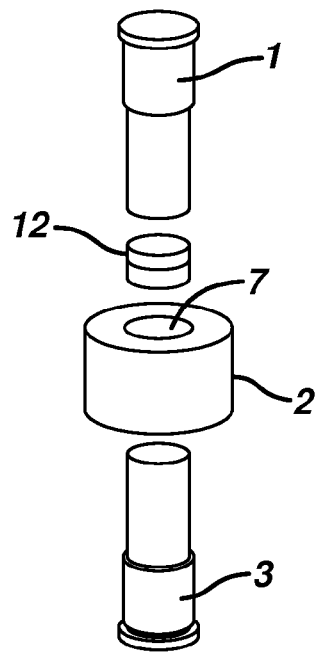

In FIGS. 2A-2H, an alternate embodiment of the invention is shown where a multilayer tablet is produced. First, powder blend 10 is filled into die platen 2 as shown in FIG. 2A. Powder blend 10 is tamped or moved down into die platen 2 by upper forming tool 1 as shown in FIG. 2B to form tablet shape 10a. Then, powder blend 11 is then filled on top of tablet shape 10a. The forming tools 1 and 3, die platen 2, tablet shape 10a and powder blend 11 are then moved to the compaction and RF heating station as shown in FIG. 2E. RF heating is accomplished as described above in FIG. 1C to produce multilayer tablet 12 as shown in FIGS. 2F and 2G. While a bi-layer tablet is shown in the drawing, additional multiple layers can be produced by adding additional powder blends to die platen 2.

Figure 3F:
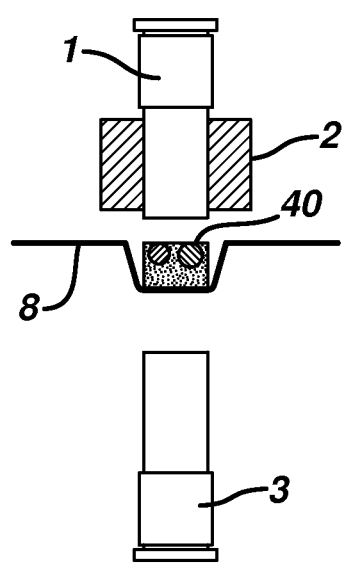
Figure 3G:
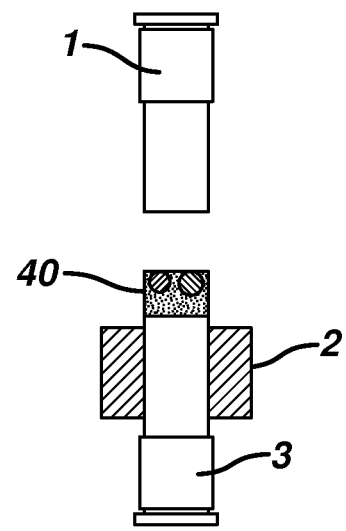

FIGS. 3A-3G show another embodiment of the invention where preformed inserts 30 and 31 are inserted into tablet shape 20a as shown in FIGS. 3A-3D. Forming tools 1 and 3, die platen 2, tablet shape 20, and preformed inserts 30 and 31 are then moved to the compaction and RF heating station as shown in FIG. 3E. RF heating is accomplished as described above in FIG. 1C to produce a multi-component tablet 40 shown in FIGS. 2F and 2G.

Figure 4A:
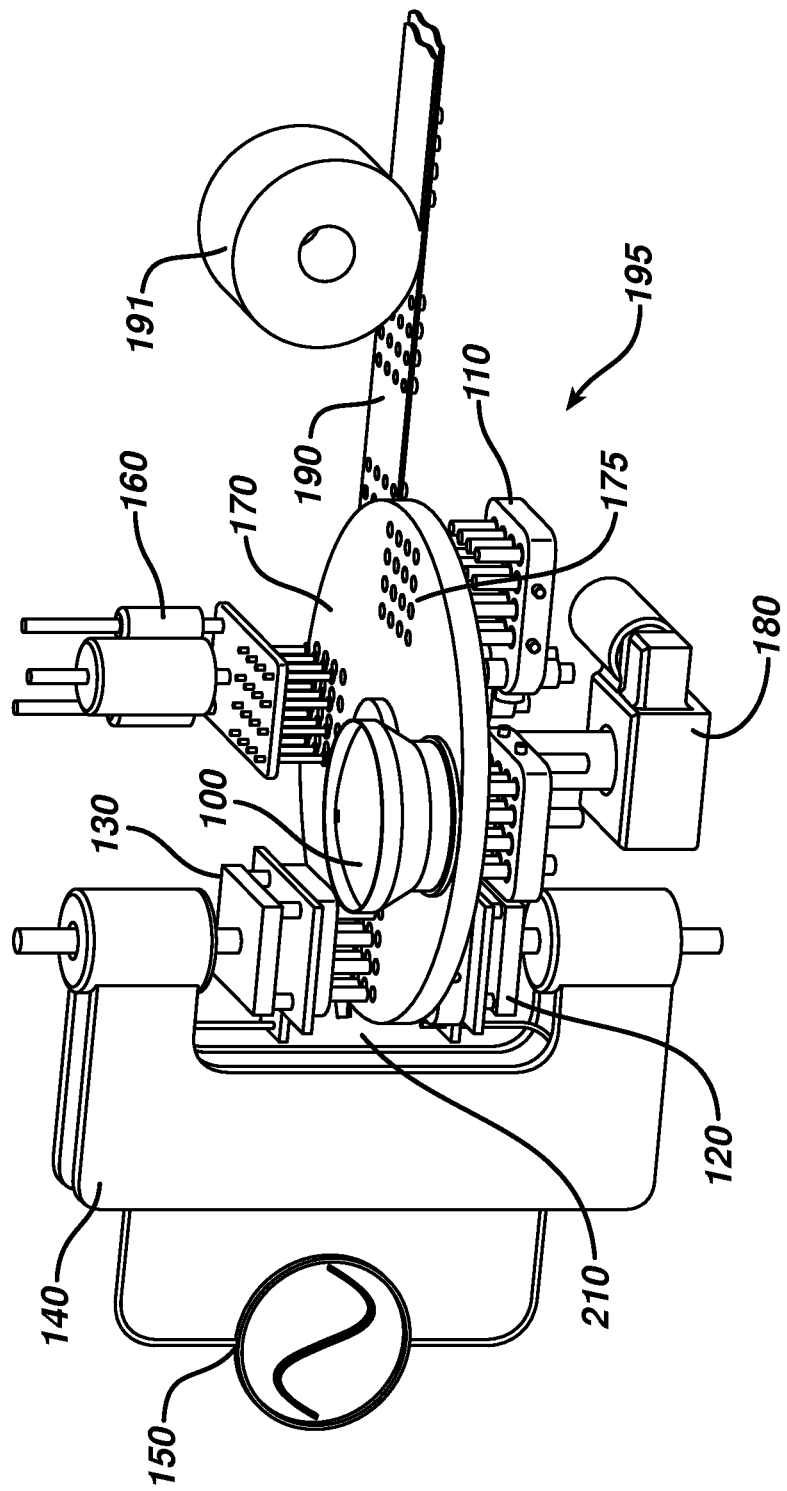
FIGS. 4A and 4B are a perspective view of a rotary indexing machine 195.
Figure 4B:
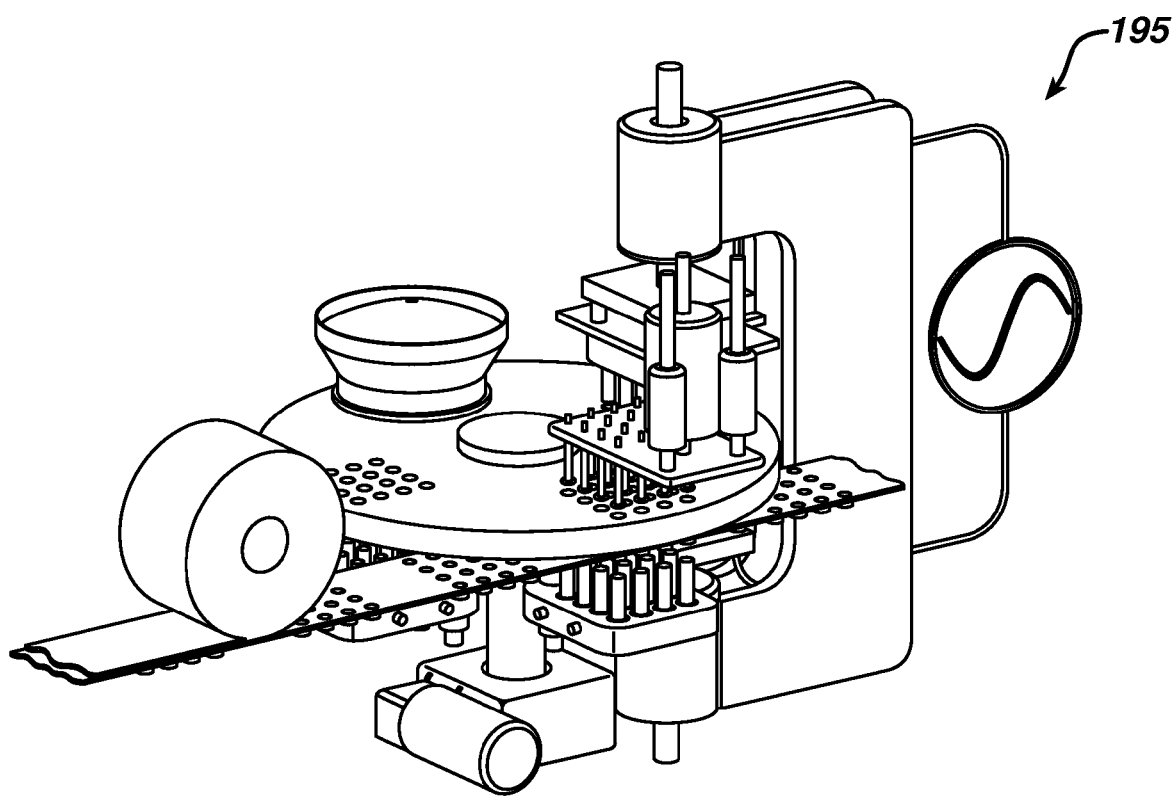

FIGS. 4A and 4B show two views of a rotary indexing machine 195 which is designed to create large quantities of tablets. In particular, the configuration of the apparatus shown is designed to manufacture fragile tablets with minimized risk of damaging them as they are moved through the various manufacturing steps. This embodiment of the invention is comprised of an indexing table 170 having four sets of die platens 175 each having sixteen cavities, powder feeder 100, RF generator 150, a machine frame 140, moving RF electrode assemblies 120 and 130, lower forming tool assembly 110, upper forming tool assembly 210, tablet ejection station 160, indexer drive system 180, blister package web 190, and blister lid material roll 191.

Figure 5A:
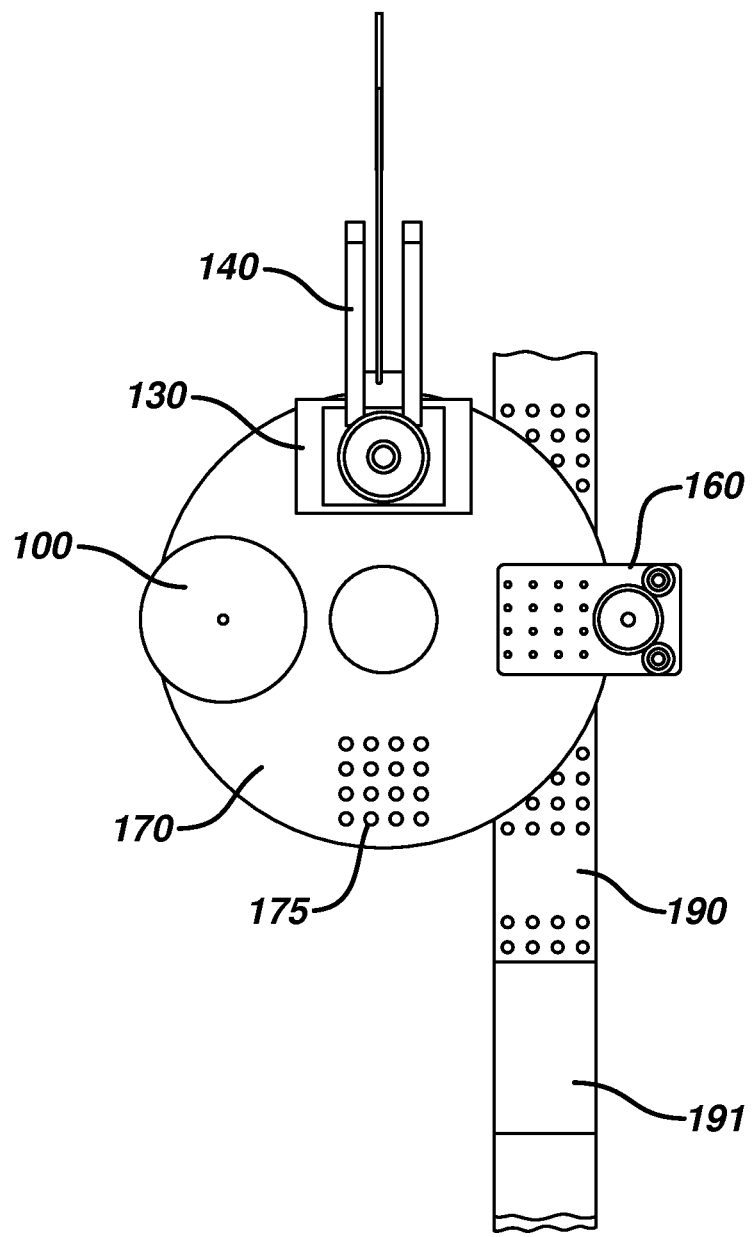
FIGS. 5A and 5B are top views of the rotary indexing machine 195 in the dwell position.
Figure 5B:
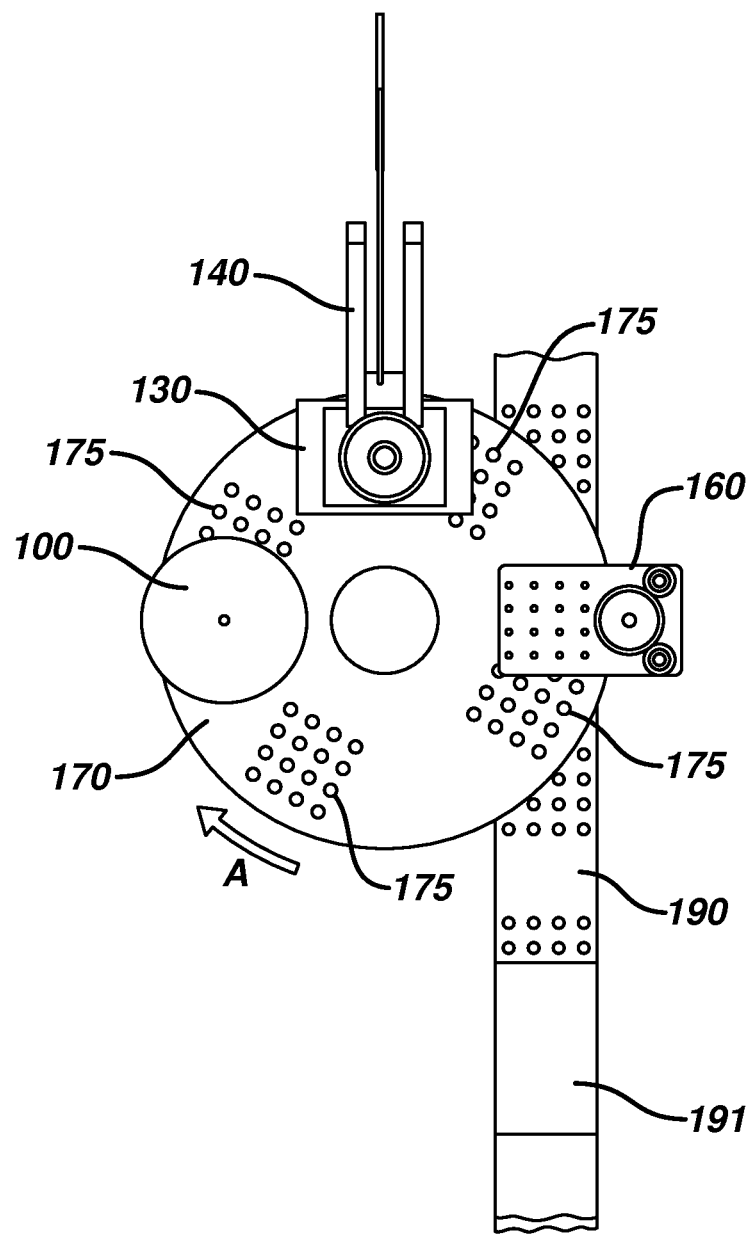
Figure 6A:
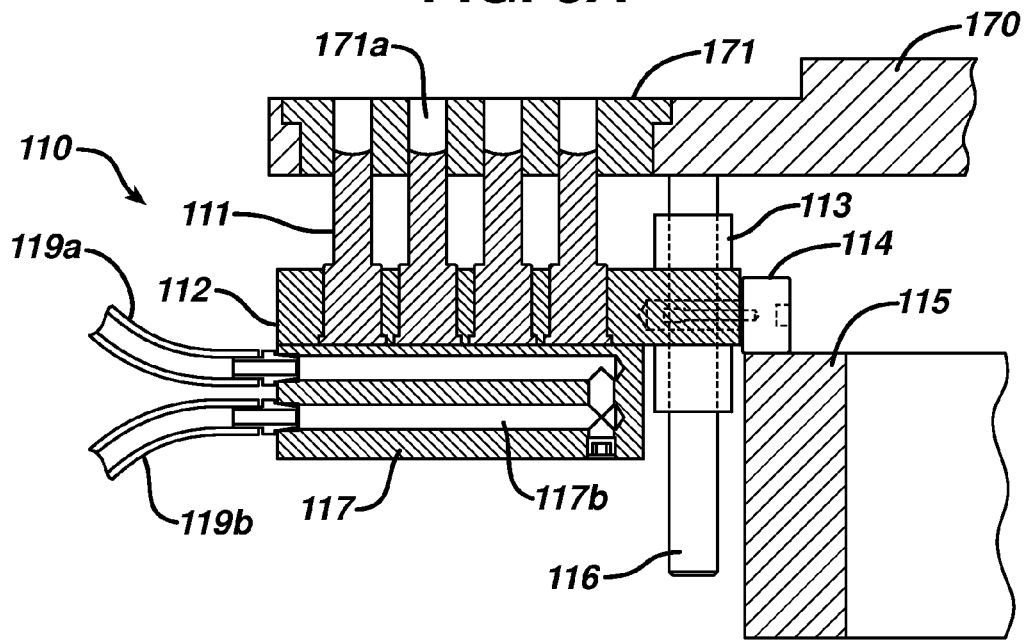
FIGS. 6A and 6B are section views of the lower forming tool assembly 110 in the start position of the manufacturing cycle.

FIG. 5A is a top view of the apparatus in the dwell position. FIG. 5B is a top view of the apparatus as the indexing table 170 rotates between stations in direction "A". FIG. 6A depicts a section view through the lower forming tool assembly 110 in a start position of the manufacturing cycle. The lower forming tools 111, which are made of an electrically conductive metallic material such as brass or stainless steel, are retained in retainer plate 112 (e.g., made of aluminum or steel). Heated block 117 is attached to the retainer plate 112 and contains fluid passages 117b. Heated (or optionally cooling) fluid is circulated through the heated block 117 by connections to flexible hoses 119a and 119b which form a supply and return circuit. Heating can also be accomplished by electric cartridge heaters or other suitable means (not shown). Attached to the retainer plate are cam-follower 114 and linear bearing 113. A guide shaft 116 is fixed to indexing table 170. The retainer plate and forming tools 111 and are moveable up or down according to the profile of barrel cam 115 which cam follower 114 rolls upon. Also shown is die platen 171, which is made of electrical and RF energy insulative material such as Teflon, UHMW, or ceramic. This is necessary to prevent a short circuit when the electrically conductive forming tools are positioned in the RF electric field in subsequent steps. The forming cavity 171a is shown empty at this stage of the process.

Figure 6B:
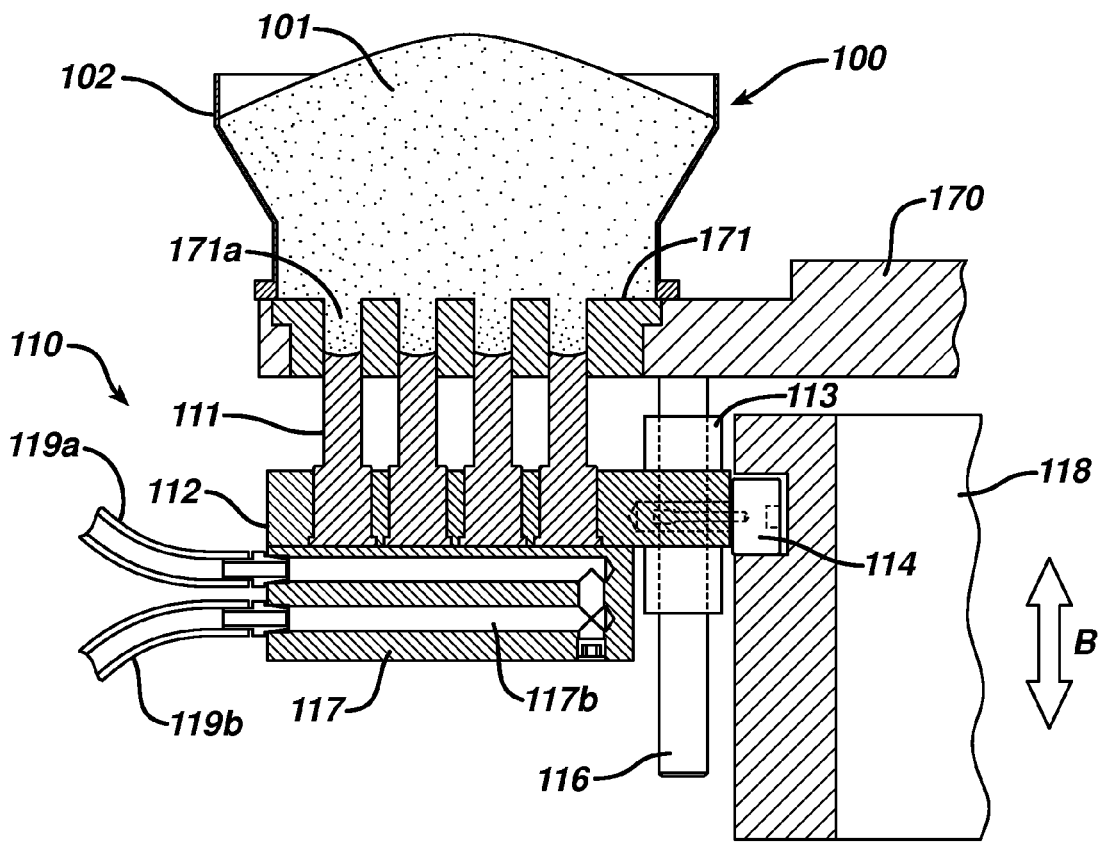

FIG. 6B depicts a section through the powder feeder station 100 of the apparatus. In this station powdered powder blend 101 is gravity fed into die platen 171. Movable cam segment 118 is adjusted up or down in direction "B" to vary the volume of the forming cavity 171a by changing the amount that the lower forming tools 111 penetrate into the die platen 171. This adjustable volume feature enables the precise dose of powdered powder blend to be selected for a desired tablet weight. When the machine indexes out of the powder feeder station, the rim of feeder 102 scrapes against the die platen 171 to create a level powder surface relative to the surface of the die platen 171.

Figure 7:
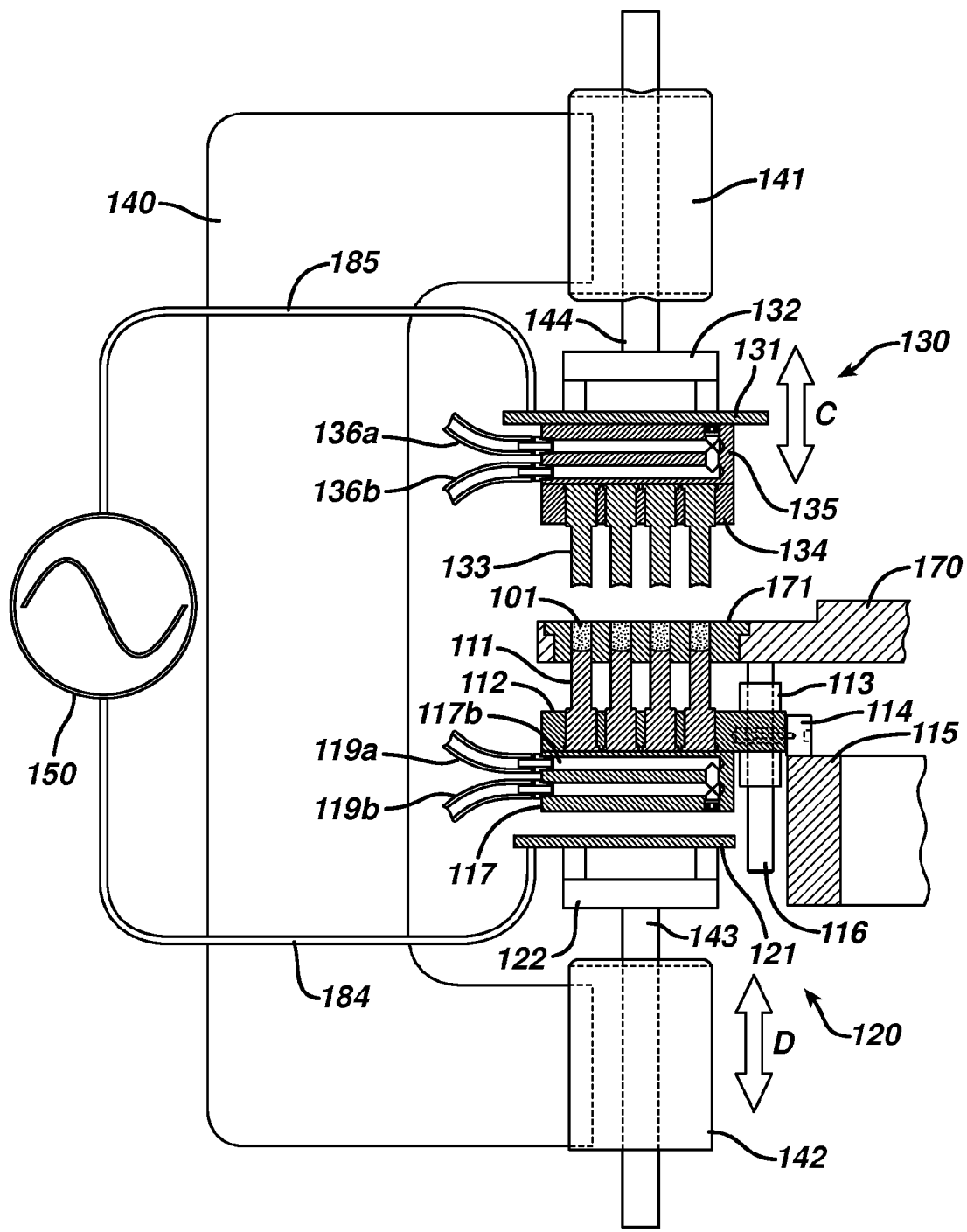
FIG. 7 is a section view through the RF station rotary indexing machine 195 prior to compacting powder blend 101.

FIG. 7 is a section view through the RF station of the apparatus. The RF generator 150 is depicted symbolically here. In one embodiment, the configuration of the RF generator 150 is a free running oscillator system. It is typically composed of a power vacuum tube (such as a triode), a DC voltage source between 1000 and 8000 volts connected across the cathode and plate (anode). A tank circuit is used to impose a sinusoidal signal upon the control grid and electrodes thereby producing the necessary frequency (typically 13.56 MHZ or 27.12 MHZ) and high voltage field. An example of such RF generator 150 is the COSMOS Model C10X16G4 (Cosmos Electronic Machine Corporation, Farmingdale, N.Y.). In another embodiment, RF energy can be provided by a 50 Ohm system composed of a waveform generator which feeds a radio frequency signal to power amplifiers which are coupled to the electrodes and the load by an impedance matching network.

In FIG. 7, a lower movable RF electrode 121 is shown, movable in direction "D". It is represented in its down position. The linear movement is generated by linear actuators which are typically devises such as air cylinders or servo motors. Two air cylinders are depicted in FIG. 7. Air cylinder bodies 141 and 142 apply pressure to guide rods 144 and 143. Moving platens 132 and 122 are connected to the guide rods and provide an electrically isolated mounting for electrode plates 131 and 121. RF generator 150 connects to the electrode plates 131 and 121 through wires 185 and 184. A movable upper RF electrode assembly 130, movable in direction "C", is shown in its up position. Upper forming tools 133, retainer plate 134, and heated block 135 are all attached to the movable RF electrode plate 131 and, consequently, move up and down with it. Powder blend 101 is within die platen 171.

Figure 8:
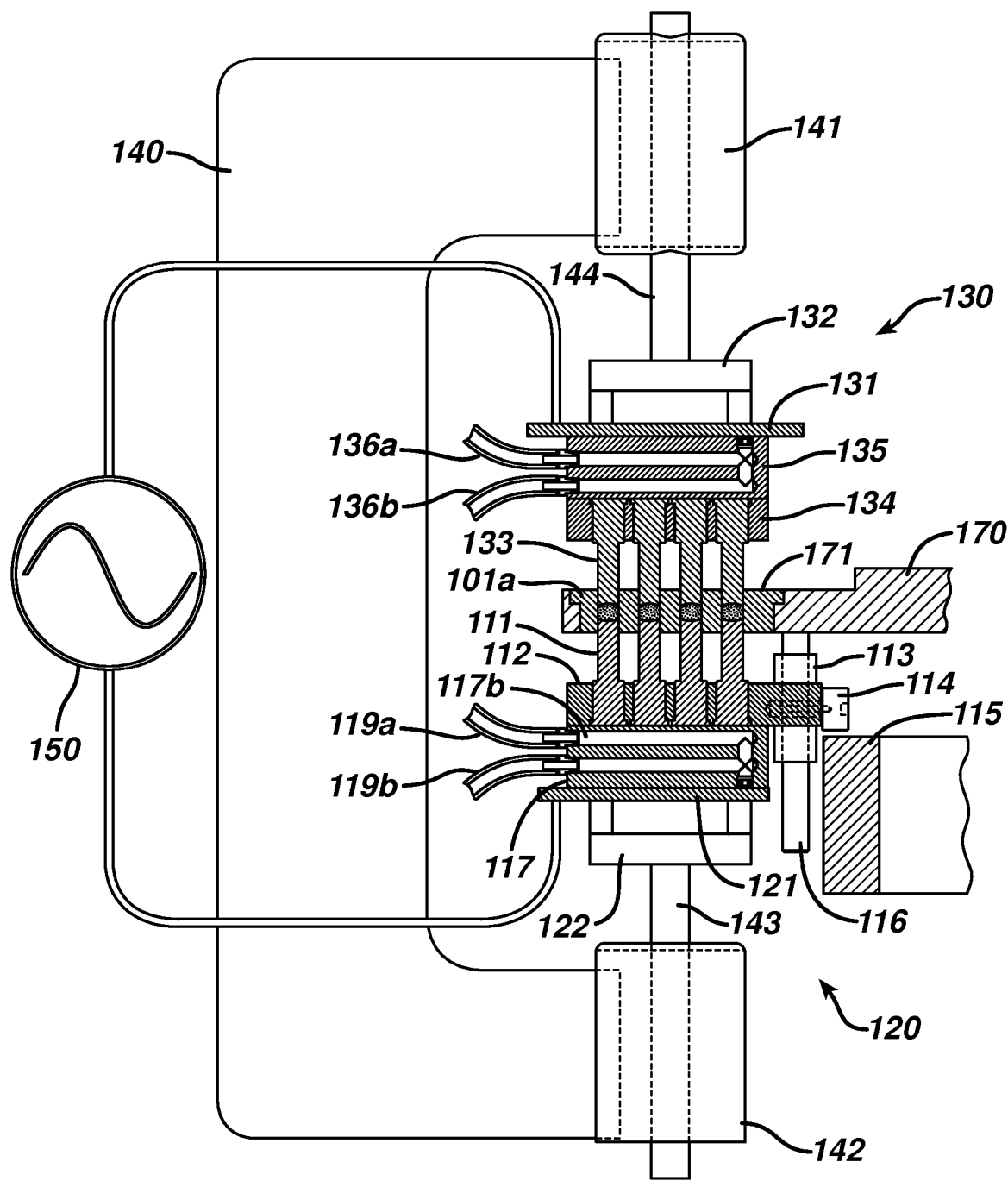

FIG. 8 is a section through the same RF station but shows the RF electrodes 131 and 121 pressing against the respective forming tool assemblies 133 and 111 to both compact and apply RF energy to powder blend 101 creating tablet 101a. After application of the RF energy is stopped, the moveable RF electrode plates retract, and the indexing plate 170, die platen 171, and lower forming tool assembly 110 are indexed to the next station.

Figure 9:
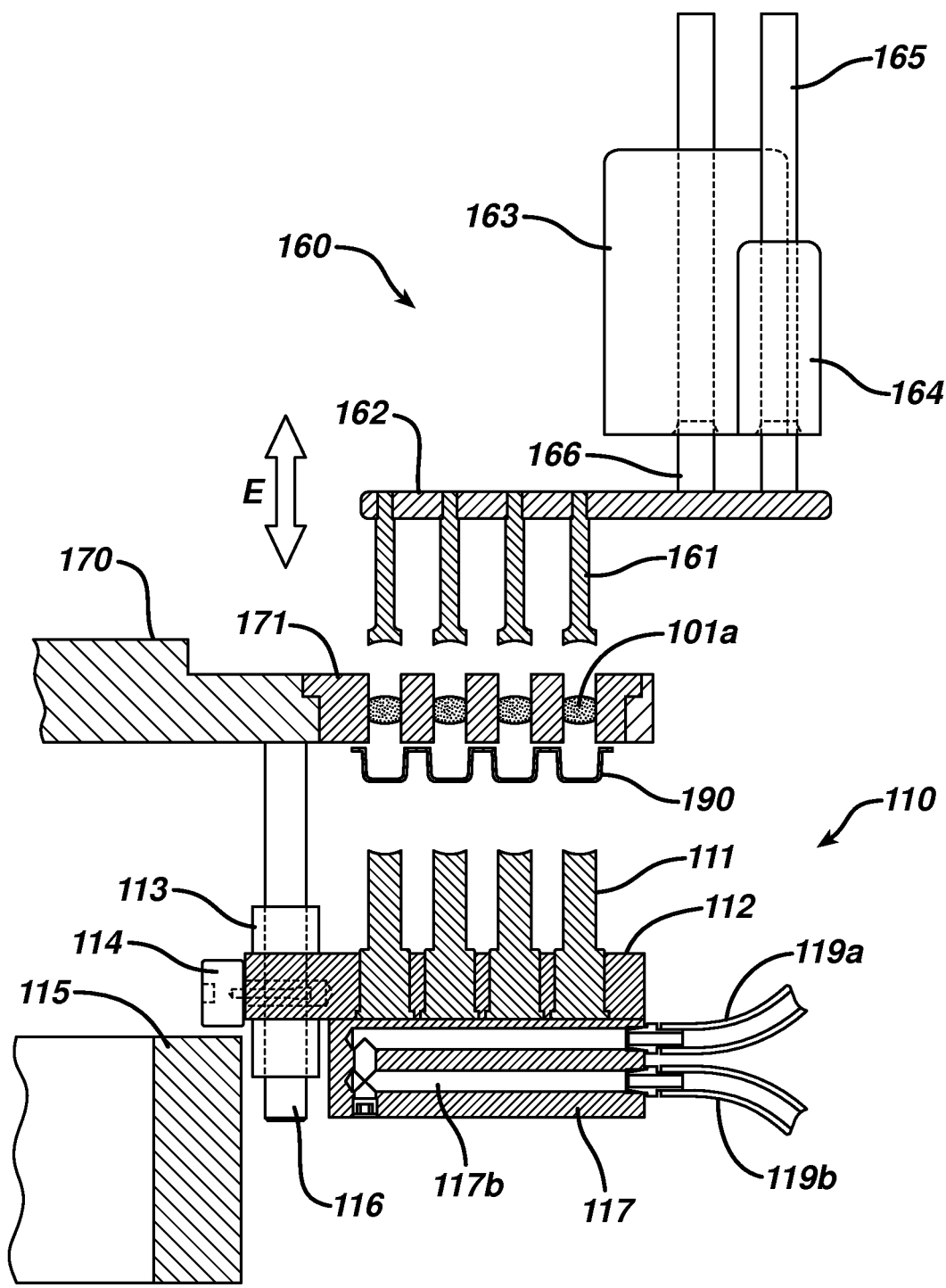
FIG. 9 is a section view through tablet ejection station 160 before tablets 101a have been ejected.

FIG. 9 is a section view through the tablet ejection station 160. Ejector pins 161 are attached to movable plate 162 (movable in the "E" direction), which is actuated by actuator assembly 163 (for example, this can be a linear servo motor or air cylinder or other suitable actuator). Actuator rod 166 connects to the movable plate 162. Linear bearing 164 and guide rod 165 provide rigidity and support for the actuator plate 162 and prevent destructive side loads created by the ejection force from acting upon actuator 163. A blister package 190 is shown below die platen 171.

Figure 10:
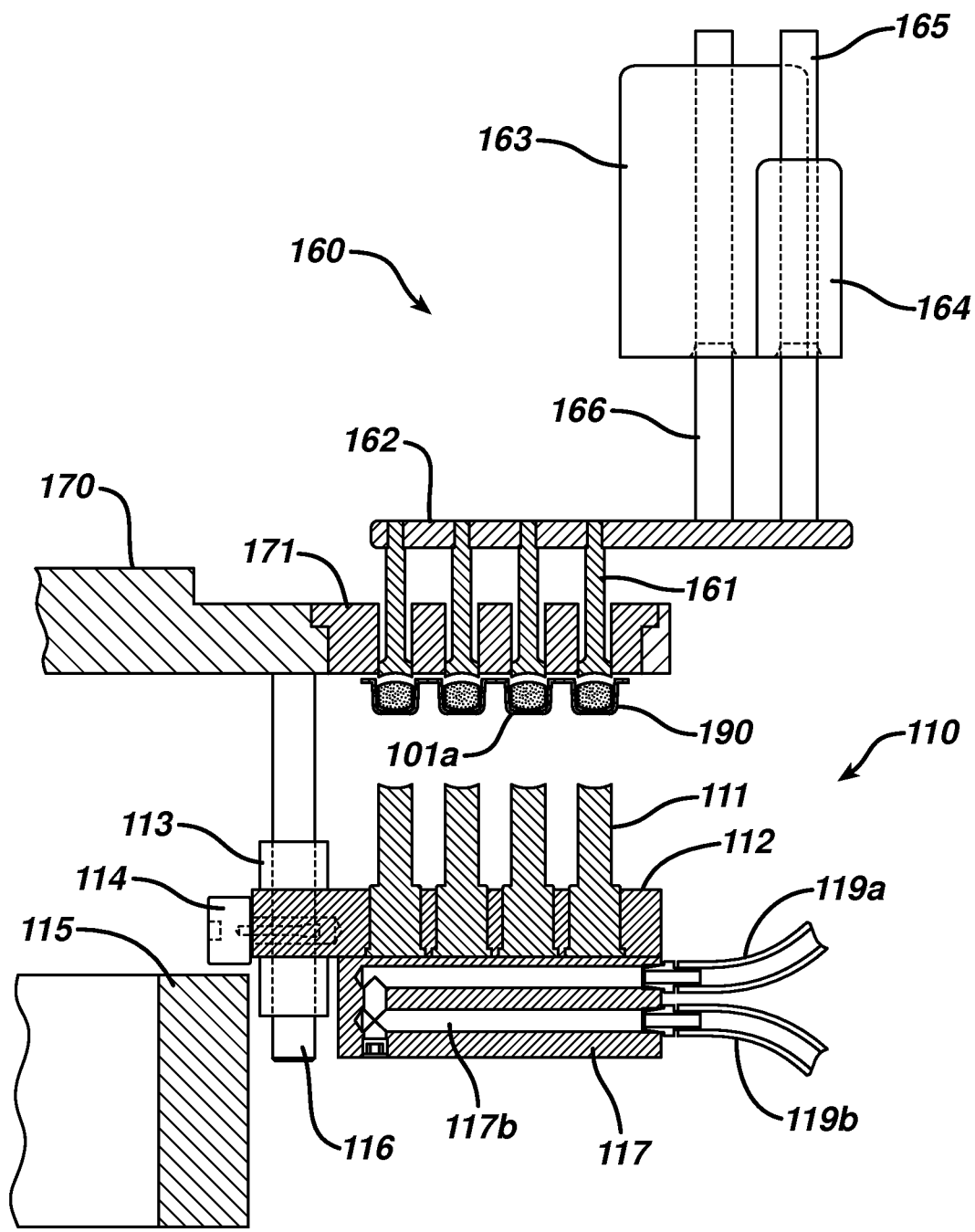
FIG. 10 is a section view through tablet ejection station 160 after tablets 101a have been ejected into blister 190.

FIG. 10 is a section through the same assembly after the ejector pins 161 have pushed finished tablets 101a through the die platen 171. This direct placement of tablet into blister helps prevent breakage that could occur while using typical means such as feeders or by dumping tablets into transport drums.

In one embodiment, a lubricant is added to forming cavity prior to the addition of the flowable powder blend. This lubricant may be a liquid or solid. Suitable lubricants include but are not limited to solid lubricants such as magnesium stearate, starch, calcium stearate, aluminum stearate and stearic acid; or liquid lubricants such as but not limited to simethicone, lecithin, vegetable oil, olive oil, or mineral oil. In certain embodiments, the lubricant is added at a percentage by weight of the tablet of less than 5 percent, e.g. less than 2 percent, e.g. less than 0.5 percent. In certain embodiments, the presence of a hydrophobic lubricant can disadvantageously compromise the disintegration or dissolution properties of a tablet. In one embodiment the tablet is substantially free of a hydrophobic lubricant. Hydrophobic lubricants include magnesium stearate, calcium stearate and aluminum stearate.

Radiofrequency Heating of Tablet Shape to Form Tablet

Radiofrequency heating generally refers to heating with electromagnetic field at frequencies from about 1 MHz to about 100 MHz. In one embodiment of the present invention, the RF-energy is within the range of frequencies from about 1 MHz to about 100 MHz (e.g., from about 5 MHz to 50 MHz, such as from about 10 MHz to about 30 MHz). The RF-energy is used to heat the binder (e.g., either directly when the meltable binder is a RF-meltable binder or indirectly when the meltable binder is not a RF meltable binder but is heated by a RF-heatable ingredient within the powder blend). The degree of compaction, the type and amount of meltable binder, and the amount of RF energy used can determine the hardness and/or type of tablet whether an oral disintegrating tablet or a soft chewable tablet is manufactured.

RF energy generators are well known in the art. Examples of suitable RF generators include, but are not limited to, COSMOS Model C10X16G4 (Cosmos Electronic Machine Corporation, Farmingdale, N.Y.).

In one embodiment, the upper and lower forming tools serve as the electrodes (e.g., they are operably associated with the RF energy source) through which the RF energy is delivered to the tablet shape. In one embodiment, there is direct contact between at least one RF electrode (e.g., forming tool) and the tablet shape. In another embodiment, there is no contact between any of the RF electrode (e.g., forming tools) and the tablet shape. In one embodiment, the RF electrodes are in direct contact with the surface of the tablet shape when the RF energy is added. In another embodiment, the RF electrodes are not in contact (e.g., from about 1 mm to about 1 cm from the surface of the tablet shape) during the addition of the RF energy.

In one embodiment, the RF energy is delivered while the tablet shape is being formed. In one embodiment, the RF energy is delivered once the tablet shape is formed. In one embodiment, the RF energy is delivered after the tablet shape has been removed from the die.

In one embodiment, the RF energy is applied for a sufficient time to soften and melt substantially all (e.g., at least 90%, such as at least 95%, such as all) of the binder within the tablet shape. In one embodiment, the RF energy is applied for a sufficient time to soften and melt only a portion (e.g., less than 75%, such as less than 50%, such as less than 25%) of the binder within the tablet shape, for example only on a portion of the tablet shape, such as the outside of the tablet shape.

Figure 11A:
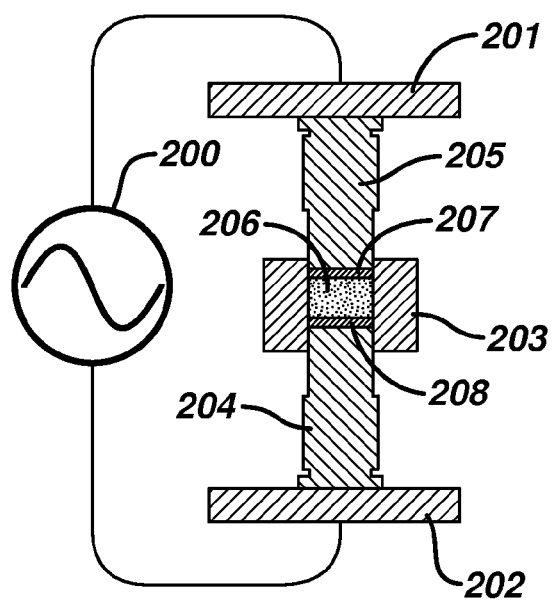
FIGS. 11A-D are cross sections of alternate embodiments of forming tools and the die platen.
Figure 11B:
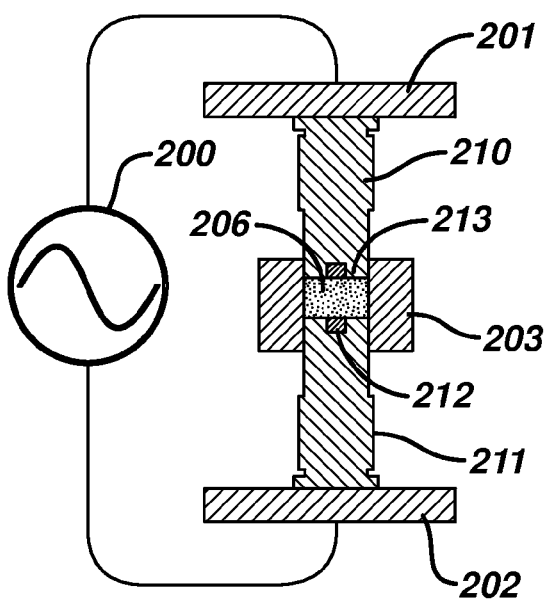
Figure 11C:
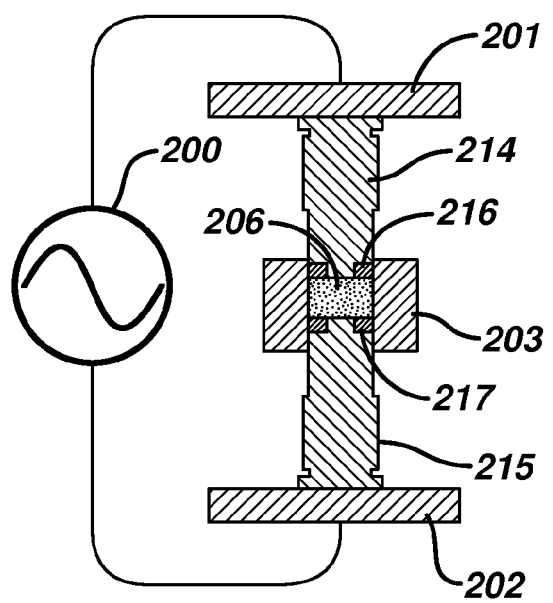
Figure 11D:
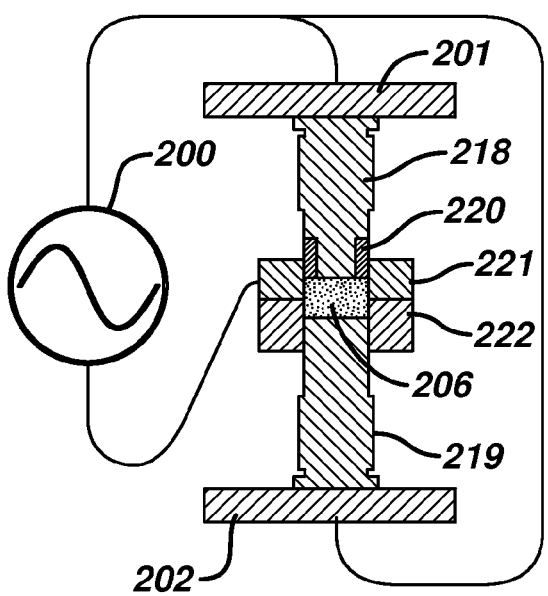

In alternate embodiments of the invention, the forming tools can be constructed to achieve localized heating effects and can also be configured to shape the electric field that is developed across the tools. FIG. 11A shows one such configuration. An RF generator 200 is connected to RF electrode plates 201 and 202. Forming tools 205 and 204 are constructed of an electrically conductive material and they have an attachment 207 and 208 which are made of electrical and RF energy insulative material such as ceramic, Teflon®, polyethylene, or high density polyethylene. Die platen 203 is also constructed of electrical and RF energy insulative material. This configuration creates greater distance between the conductive forming tools to weaken the electric field which is beneficial for producing thin tablets without the risk of an electric arc forming which would damage the product and tooling. FIG. 11B depicts a similar configuration but with forming tools 210 and 211 that, respectively, have a recess containing insert 213 and 212 which are made of electrical and RF energy insulative material. This geometry will produce a tablet with lesser heating in the area where the inserts 213 and 212 are located since the electric field is weaker due to the greater distance between the conductive portions of 211 and 210. FIG. 11C is similar to FIG. 11B only the geometry is reversed so the tablet formed by this configuration will have a greater heating effect at the center since the inserts 216 and 217 are at the periphery of respective forming tools 214 and 215. FIG. 11D depicts another embodiment whereby the die platen is constructed of an electrically conductive component 221 and electrically insulating component 222, which is made of electrical and RF energy insulative material. Forming tools 219 and 218 are electrically conductive, but forming tool 218 further contains second electrically insulating component 220 around the surface of upper forming tool 218 which contact tablet shape 206. This configuration creates an electric field and associated zones of heating that is preferential to the conductive portions of the die platen.

Figure 12A:
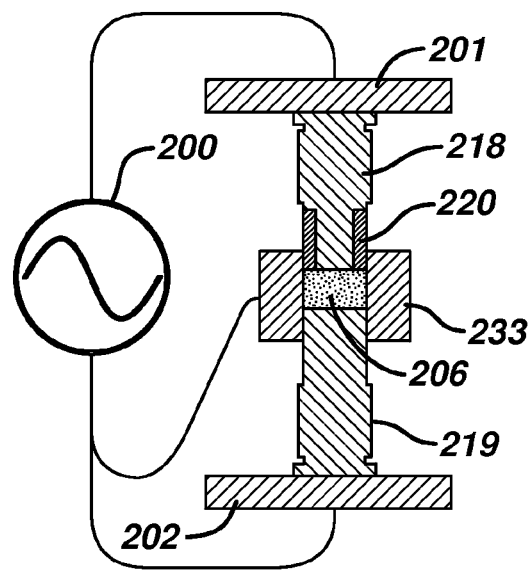
FIGS. 12A-D are cross sections of alternate embodiments of forming tools and the die platen.
Figure 12B:
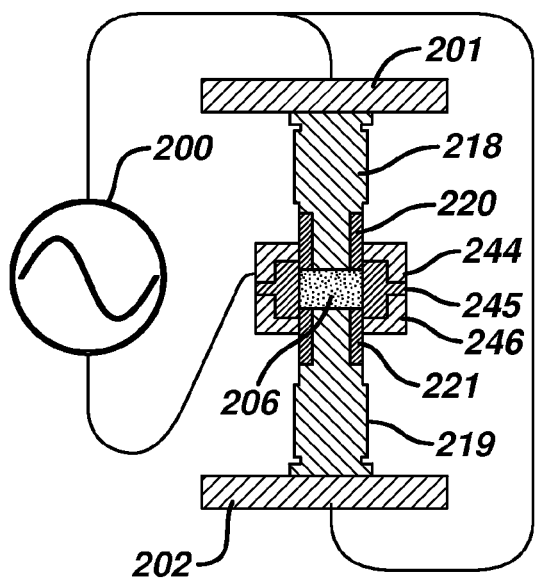
Figure 12C:
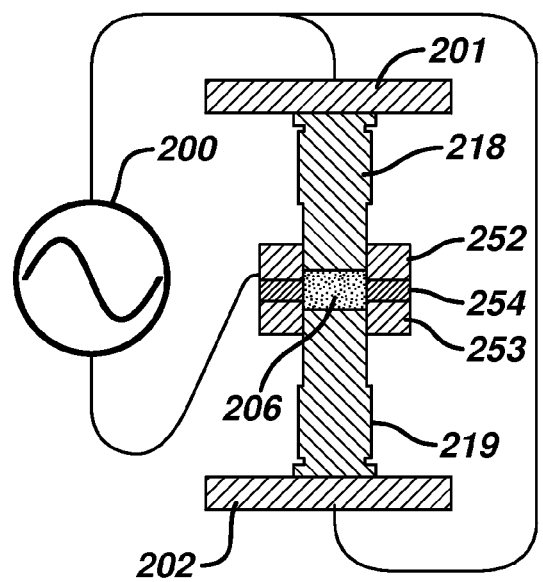
Figure 12D:
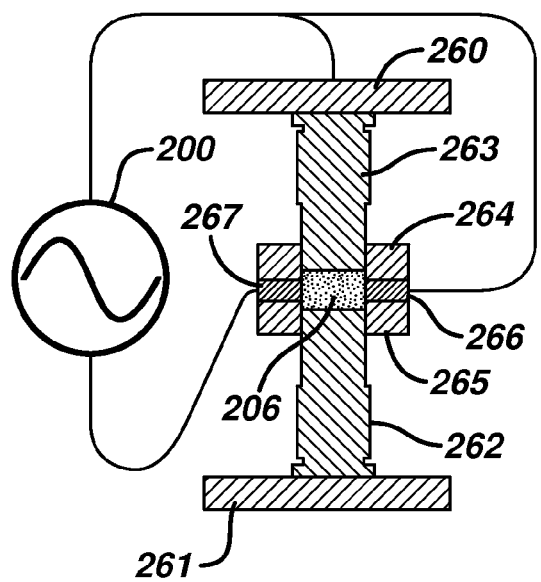

FIG. 12A is similar to FIG. 11D except the die platen 233 in this embodiment is constructed entirely of electrically conductive material. FIGS. 12B and 12C depict two embodiments where the die platen comprises a respective center portion 245 and 254 that are electrically conductive and respective outer portions 244/246 and 252/253 is are made of electrical and RF energy insulative material. FIG. 12B further includes insulating component 220 around the surface of lower forming tool 219. FIG. 12D is a further embodiment where the forming tools 263 and 262 are made of electrical and RF energy insulative material. The die platen portions 264 and 265 are made of electrical and RF energy insulative material, but there are two respective electrically conductive portions 267 and 266 which are attached to the RF generator circuit 200. In this configuration, the electric field is applied in the horizontal direction across the tablet shape 206.

Figure 13A:
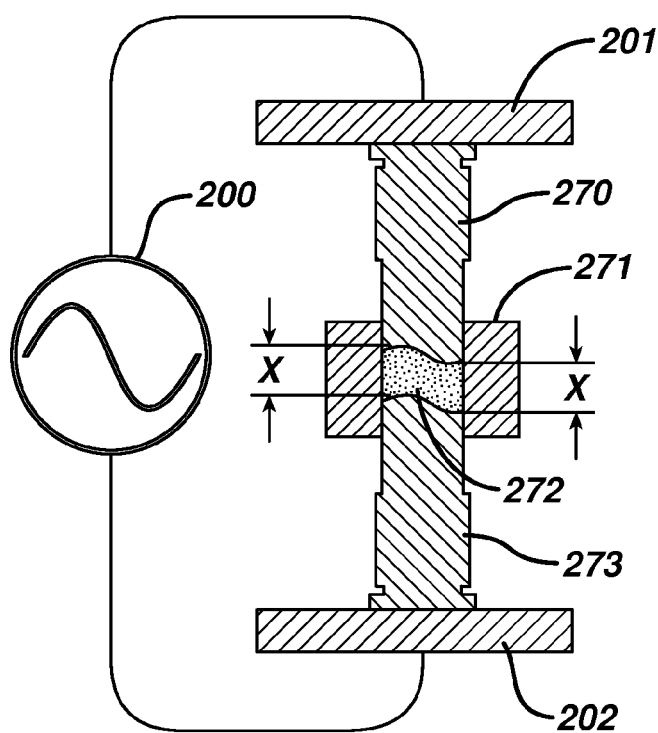
FIG. 13A is a cross section of forming tools having a wave-shaped surface.
Figure 13B:
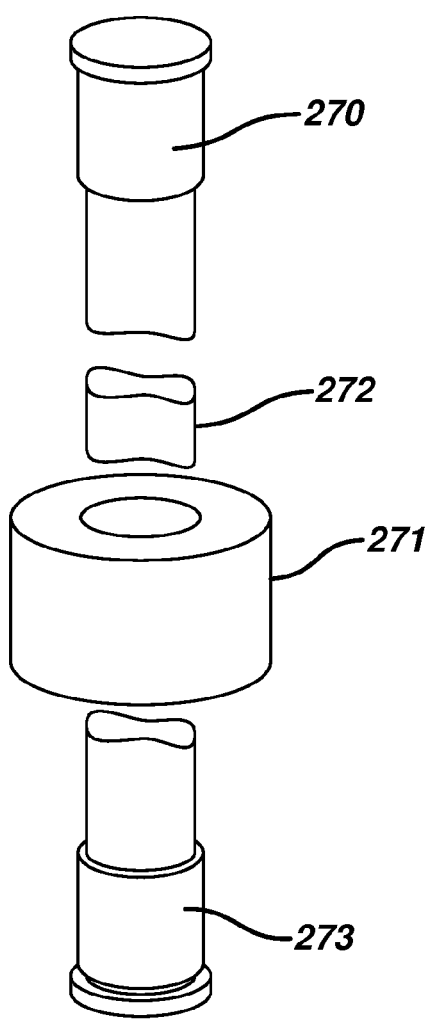
FIG. 13B is a perspective view of forming tools having a wave-shaped surface.

As described above, the distance between conductive portions of the forming tool has a strong effect on field strength and heating effect. To create a tablet with uniform heating and texture, a forming tool that is constructed with equidistant spacing is desirable. FIGS. 13A and 13B depict such a configuration. In this embodiment, a wave-shaped forming tools 270 and 273 are shown to create a tablet 272 within die platen 271 with a unique appearance. The profiles of the forming tool surfaces are equidistant as shown by dimension "X".

Figure 14:
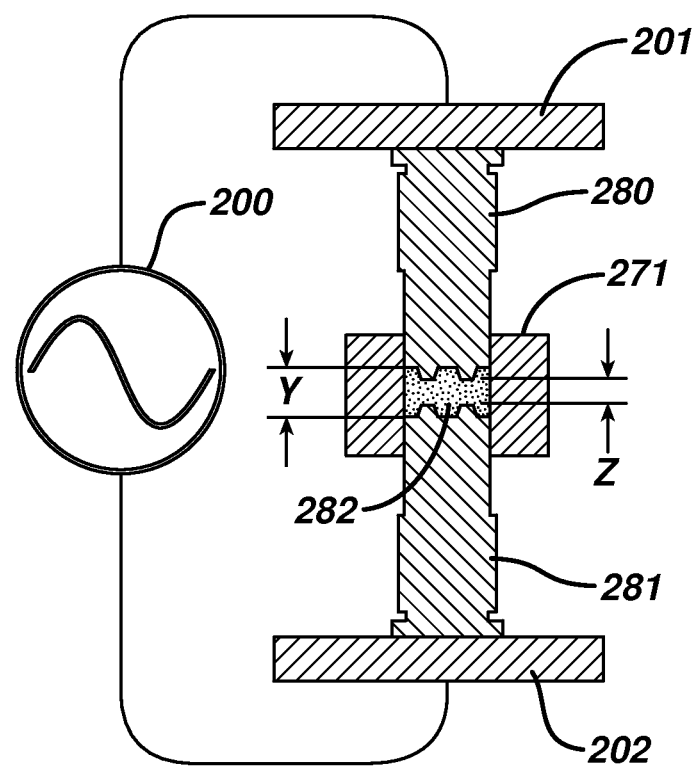
FIG. 14 is a cross section of forming tools having protrusions at the surface.

FIG. 14 is an embodiment wherein a non-uniform heating is used to manufacture tablet 282. In this embodiment, a tablet with hard and soft zones is created. The forming tools 280 and 281 are made with protrusions at the surface that create high field strength (resulting in greater heating) where they are closest together (shown by the dimension "Z") and weaker field strength (resulting in lesser heating) where they are further apart (shown by the dimension "Y").

In one embodiment, to help reduce sticking, the tablet is cooled within the forming cavity to cool and/or solidify the binder. The cooling can be passive cooling (e.g., at room temperature) or active cooling (e.g., coolant recirculation cooling). When coolant recirculation cooling is used, the coolant can optionally circulate through channels inside the forming tools (e.g., punches or punch platen) and/or die or die platen (e.g., as discussed above in FIGS. 6A and 6B). In one embodiment, the process uses a die platen having multiple die cavities and upper and lower punch platens having multiple upper and lower punched for simultaneous forming of a plurality of tablets wherein the platens are actively cooled.

In one embodiment, there is a single powder blend forming the tablet shape which is then heated with the RF energy. In another embodiment, the tablet is formed of at least two different powder blends, at least one powder blend being RF-curable and at least one formulation being not RF-curable. When cured with RF energy, such tablet shape develops two or more dissimilarly cured zones. In one embodiment, the outside area of the tablet shape is cured, while the middle of the tablet shape is not cured. By adjusting the focus of the RF heating and shape of the RF electrodes, the heat delivered to the tablet shape can be focused to create customized softer or harder areas on the finished tablet.

In one embodiment the RF energy is combined with a second source of heat including but not limited to infrared, induction, or convection heating. In one embodiment, the addition of the second source of heat is particularly useful with a secondary non-RF-meltable binder present in the powder blend.

Microwave Heating of Tablet Shape to Form Tablet

In one embodiment, microwave energy is used in place of radiofrequency energy to manufacture the dosage form (e.g., tablet). Microwave heating generally refers to heating with electromagnetic field at frequencies from about 100 MHz to about 300 GHz. In one embodiment of the present invention, the RF-energy is within the range of frequencies from about 500 MHz to about 100 GHz (e.g., from about 1 GHz to 50 GHz, such as from about 1 GHz to about 10 GHz). The microwave energy is used to heat the binder (e.g., either directly when the meltable binder is susceptible to microwave energy ("microwave meltable binder") or indirectly when the meltable binder is not a microwave meltable binder but is heated by a microwave heatable ingredient within the powder blend. In such an embodiment, a microwave energy source and microwave electrodes are used in the machine used to manufacture the dosage form.

Inserts within Tablet Shape

In one embodiment, an insert is incorporated into the tablet shape before the RF energy is delivered. Examples include solid compressed forms or beads filled with a liquid composition. Such incorporation of an insert is depicted in FIGS. 3A-3G.

In one embodiment the pharmaceutically active agent is in the form of a gel bead, which is liquid filled or semi-solid filled. The gel bead(s) are added as a portion of the powder blend. In one embodiment, the tablet of this invention has the added advantage of not using a strong compaction step, allowing for the use of liquid or semisolid filled particles or beads which are deformable since they will not rupture following the reduced pressure compaction step. These bead walls may contain gelling substances such as: gelatin; gellan gum; xanthan gum; agar; locust bean gum; carrageenan; polymers or polysaccharides such as but not limited to sodium alginate, calcium alginate, hypromellose, hydroxypropyl cellulose and pullulan; polyethylene oxide; and starches. The bead walls may further contain a plasticizer such as glycerin, polyethylene glycol, propylene glycol, triacetin, triethyl citrate and tributyl citrate. The pharmaceutically active agent may be dissolved, suspended or dispersed in a filler material such as but not limited to high fructose corn syrup, sugars, glycerin, polyethylene glycol, propylene glycol, or oils such as but not limited to vegetable oil, olive oil, or mineral oil.

In one embodiment, the insert is substantially free of RF-absorbing ingredients, in which case application of the RF energy results in no significant heating of the insert itself. In other embodiments, the insert contains ingredients and are heated upon exposure to RF energy and, thus, such inserts can be used to soften or melt the meltable binder.

Multi-Layer Tablet

In certain embodiments, the tablet includes at least two layers, e.g., with different types and/or concentrations of binders and/or other ingredients or different concentrations of pharmaceutically active agents. Such an embodiment is shown in FIGS. 2A-2D. In one embodiment, the tablet includes two layers, one layer having orally disintegrating properties and another layer being chewable or swallowable. In one embodiment, one layer has a meltable binder and another layer does not have a meltable binder. In one embodiment one layer is compacted at higher compaction force versus the other layer. In one embodiment, both layers contain same amount of the meltable binder, but have different amount of pharmaceutically active agents and/or other excipients. In one embodiment, all properties of the two layers are identical but the colors of the two layers are different.

Effervescent Couple

In one embodiment, the powder blend further contains one or more effervescent couples. In one embodiment, effervescent couple contains one member from the group consisting of sodium bicarbonate, potassium bicarbonate, calcium carbonate, magnesium carbonate, and sodium carbonate, and one member selected from the group consisting of citric acid, malic acid, fumaric acid, tartaric acid, phosphoric acid, and alginic acid.

In one embodiment, the combined amount of the effervescent couple(s) in the powder blend/tablet is from about 2 to about 20 percent by weight, such as from about 2 to about 10 percent by weight of the total weight of the powder blend/tablet.

Orally Disintegrating Tablet

In one embodiment, the tablet is designed to disintegrate in the mouth when placed on the tongue in less than about 60 seconds, e.g. less than about 45 seconds, e.g. less than about 30 seconds, e.g. less than about 15 seconds.

In one embodiment, the tablet meets the criteria for Orally Disintegrating Tablets (ODTs) as defined by the draft Food and Drug Administration guidance, as published in April, 2007. In one embodiment, the tablet meets a two-fold definition for orally disintegrating tablets including the following criteria: 1) that the solid tablet is one which contains medicinal substances and which disintegrates rapidly, usually within a matter of seconds, when placed upon the tongue and 2) be considered a solid oral preparation that disintegrates rapidly in the oral cavity, with an in vitro disintegration time of approximately 30 seconds or less, when based on the United States Pharmacopeia (USP) disintegration test method for the specific medicinal substance or substances.

Additional Edible Portion

In one embodiment, the tablet is contained next to another edible form. In one embodiment, this edible form is a hard candy or compressed ring that holds the powder blend during compaction and/or the RF heating step.

In one embodiment, the outer hard candy form may be made using uniplast rolling or roping and subsequent cutting and stamping, as well as depositing into molds. The hard candy portion contains one or more sugars selected from the group consisting of isomalt, sucrose, dextrose, corn syrup, lactitol, and lycasin. In one embodiment, the hard candy portion contains at least 50% (such as at least 75%, such as at least 90%) by weight of such sugar(s).

In one embodiment, the outer edible form contains a pharmaceutically active agent and the inner tablet contains a second portion of the same pharmaceutically active agent that is in the outer edible form. In one embodiment, the outer edible form contains a pharmaceutically active agent and the inner tablet contains a different pharmaceutically active agent than that in the outer edible form. In one embodiment, the outer edible form disintegrates at a rate of at least 10 times, such as at least 20 times, the rate of the inner tablet. The first and second portions can be the same or different.

In one embodiment, the tablet having an outer edible form and an inner tablet is coated with an immediate release sugar coating or film coating. In one embodiment, to produce such a tablet, the step following the fusing (heating) and subsequent cooling of the tablet would involve further sugar or film coating in a coating pan.

Hardness/Density of Tablet Shape/Tablet

In one embodiment, the tablet is prepared such that the tablet is relatively soft (e.g., capable of disintegrating in the mouth or being chewed). In one embodiment, the hardness of the tablet is preferably less than about 3 kiloponds per square centimeter ($kp/cm^2$) (e.g., less than about 2 $kp/cm^2$, such as less than about 1 $kp/cm^2$).

Hardness is a term used in the art to describe the diametral breaking strength as measured by conventional pharmaceutical hardness testing equipment, such as a Schleuniger Hardness Tester. In order to compare values across different size tablets, the breaking strength must be normalized for the area of the break. This normalized value, expressed in $kp/cm^2$, is sometimes referred in the art as tablet tensile strength. A general discussion of tablet hardness testing is found in Leiberman et al., Pharmaceutical Dosage Forms—Tablets, Volume 2, 2.sup.nd ed., Marcel Dekker Inc., 1990, pp. 213-217, 327-329.

A more preferred test for hardness of the tablet of the present invention relies upon a Texture Analyzer TA-XT2i that is fitted with a 7 millimeter diameter flat faced probe and setup to measure and report compression force in grams. The probe moves at 0.05 millimeters per second to a depth of penetration of 2 millimeters. The maximum compression force is recorded. In one embodiment, the measured forces recorded for tablets made in accordance with the present invention are less than 10,000 grams (e.g., less than about 1000 grams, such as less than about 700 grams. In one embodiment, the measured forces recorded for tablets made in accordance with the present invention ranges from about 100 grams to about 6000 grams, such as from about 100 grams to about 1000 grams, such as from about 75 grams to about 700 grams) with a deviation of ±50 grams. In another embodiment the measured forces recorded for tablets is less than 700 grams.

In one embodiment, the density of the tablet is less than about 2 g/cc (e.g., less than about 0.9 g/cc, such as less than about 0.8 g/cc, such as less than about 0.7 g/cc). In one embodiment, the difference in the density of the powdered material following the compaction step is less than about 40 percent (e.g., less than about 25 percent, such as less than about 15 percent).

Tablets Coatings

In one embodiment, the tablet includes an additional outer coating (e.g., a translucent coating such as a clear coating) to help limit the friability of the tablet. Suitable materials for translucent coatings include, but are not limited to, hypromellose, hydroxypropylcellulose, starch, polyvinyl alcohol, polyethylene glycol, polyvinylalcohol and polyethylene glycol mixtures and copolymers, and mixtures thereof. Tablets of the present invention may include a coating from about 0.05 to about 10 percent, or about 0.1 to about 3 percent by weight of the total tablet.

Surface Treating of the Dosage Form

In one embodiment, the surface of the dosage form shape and/or the dosage form (e.g., tablet shape and/or tablet) is further treated with energy (e.g., convection, infrared, or RF energy) to soften or melt the material on the surface of the dosage form and then cooled or allowed to cool to further smooth the texture, enhance the gloss of surface of the dosage form, limit the friability of the dosage form, and/or provide a mark for identification. In one embodiment, the surface of the dosage form is further exposed to infrared energy wherein the majority (at least 50 percent, such as least 90 percent, such as at least 99 percent) of the wavelength of such infrared energy is from about 0.5 to about 5 micrometers such as from about 0.8 to about 3.5 micrometers (e.g., by use of a wavelength filter). In one embodiment, the infrared energy source is a quartz lamp with a parabolic reflector (e.g., to intensify the energy) and a filter to remove unwanted frequencies. Examples of such infrared energy sources include the SPOT IR 4150 (commercially available from Research, Inc., Eden Prairie, Minn.).

Use of Tablet

The tablets may be used as swallowable, chewable, or orally disintegrating tablets to administer the pharmaceutically active agent.

In one embodiment, the present invention features a method of treating an ailment, the method including orally administering the above-described tablet wherein the tablet includes an amount of the pharmaceutically active agent effective to treat the ailment. Examples of such ailments include, but are not limited to, pain (such as headaches, migraines, sore throat, cramps, back aches and muscle aches), fever, inflammation, upper respiratory disorders (such as cough and congestion), infections (such as bacterial and viral infections), depression, diabetes, obesity, cardiovascular disorders (such as high cholesterol, triglycerides, and blood pressure), gastrointestinal disorders (such as nausea, diarrhea, irritable bowel syndrome and gas), sleep disorders, osteoporosis, and nicotine dependence.

In one embodiment, the method is for the treatment of an upper respiratory disorder, wherein the pharmaceutically active agent is selected from the group of phenylephrine, cetirizine, loratadine, fexofenadine, diphenhydramine, dextromethorphan, chlorpheniramine, chlophedianol, and pseudoephedrine.

In this embodiment, the "unit dose" is typically accompanied by dosing directions, which instruct the patient to take an amount of the pharmaceutically active agent that may be a multiple of the unit dose depending on, e.g., the age or weight of the patient. Typically the unit dose volume will contain an amount of pharmaceutically active agent that is therapeutically effective for the smallest patient. For example, suitable unit dose volumes may include one tablet.

EXAMPLES

Specific embodiments of the present invention are illustrated by way of the following examples. This invention is not confined to the specific limitations set forth in these examples.

Example 1

Manufacture of Powder Blend Containing Loratadine

The loratadine powder blend for an orally disintegrating tablet, containing the ingredients of Table 1, is manufactured as follows:

TABLE 1

Loratadine Powder Blend Formulation

| Ingredient | G/Batch | Mg/Tablet |
|---|---|---|
| Dextrose Monohydrate | 45.18 | 120.0 |
| Loratadine | 3.765 | 10.0 |
| Polyethylene Glycol 4000[1] | 24.475 | 65.0 |
| Maltodextrin[2] | 15.062 | 40.0 |
| Red Colorant | 0.028 | 0.075 |
| Simethicone DC100[3] | 5.648 | 15.0 |
| Sucralose USP | 1.13 | 3.0 |
| Polyethylene Oxide | 1.883 | 5.0 |
| Mint Flavor | 2.824 | 7.5 |
| Total | 100 | 265.575 |

[1]Commercially available from Clariant PF in Rothausstr, Switzerland
[2]Commercially available from National Starch in Bridgewater, NJ
[3]Commercially available from SPI Pharma in Wilmington, DE First, the sucralose, colorant, and flavor were placed together into a 500 cc sealable plastic bottle. The mixture was then blended end-over-end manually for approximately 2 minutes. The resulting mixture, the dextrose monohydrate, loratadine, and the polyethylene oxide were then added to another 500 cc sealable plastic bottle and mixed end-over-end manually for approximately 5 minutes. The resulting mixture was then added to a planetary bowl mixer, and the simethicone DC100 was added and mixed for approximately 3 minutes. Lastly, the polyethylene glycol 4000 and the maltodextrin were added to the mixture and mixed for approximately 3 minutes.

Example 2

Manufacture of Orally Disintegrating Tablet Containing Loratadine

A portion of the powder blend from Example 1 was placed into a ½ inch diameter forming cavity of an electrically insulative Teflon die platen. The powder blend was then tamped between an upper and lower flat-faced metal forming tools into a shape conformal to the surface of the forming tools. The tamping pressure was typically between 10 and approximately 50 psi of pressure. The forming tools, die platen and tablet shape were then placed between the upper RF electrode and lower RF electrode powered by an RF heating unit using a COSMOS Model C10X16G4 (Cosmos Electronic Machine Corporation, Farmingdale, N.Y.) RF generator having an output of 4 KW of power, frequency of 27 MHz, and the vacuum capacitor is set at 140. The forming tools are heated with reciculating water at a temperature of 57° C. The upper RF electrode was brought into contact with the upper forming tool and the lower RF electrode is brought into contact with lower forming tool. The RF heating unit was energized for 2 to 5 seconds. The resulting tablet was then ejected from the die platen using the lower forming tool.

Example 3

Manufacture of Orally Disintegrating Tablet Containing Diphenhydramine

The diphenhydramine powder blend for an orally disintegrating tablet, containing the ingredients of Table 2, was manufactured as follows. The sucralose, yellow colorant, flavors, polyethylene glycol and maltodextrin from the formula in Table 2 were passed through a 20 mesh screen. The sieved materials were placed into a 500 cc plastic bottle and blended end over end with the remaining materials in Table 2. The powder blend was placed into the forming cavity, tamped, and activated with RF energy as described in Example 2 for approximately 2 to 5 seconds to form the orally disintegrating tablet and subsequently removed from the die platen.

TABLE 2

Powder Blend Formulation Containing Diphenhydramine (DPH)

| Ingredient | G/Batch | Mg/Tablet |
| --- | --- | --- |
| Dextrose Monohydrate | 304.11 | 219.0 |
| Diphenhydramine (Coated)[3] | 49.57 | 35.70 |
| Polyethylene Glycol 8000[1] | 44.16 | 31.80 |
| Maltodextrin[2] | 88.46 | 63.70 |
| Yellow Colorant | 0.78 | 0.56 |
| Orange Flavor | 1.65 | 1.19 |
| Vanilla Flavor | 2.21 | 1.59 |
| Sucralose USP | 1.11 | 0.80 |
| Citric Acid USP Anhydrous | 7.96 | 5.73 |
| Total | 500.00 | 360.07 |

[1]Commercially available from Clariant PF in Rothausstr, Switzerland
[2]Commercially available from National Starch in Bridgewater, NJ
[3]Encapsulated Diphenhydramine coated utilizing cellulose acetate and polymethacrylate, utilizing process outlined in U.S. Pat. No. 5,997,905 incorporated herein by reference Example 4

Manufacture of Orally Disintegrating Tablet Placebo Containing Dextrose Monohydrate The placebo powder blend for an orally disintegrating tablet, containing the ingredients of Table 3, was manufactured as follows. The sucralose, yellow colorant, flavors, polyethylene glycol and maltodextrin from the formula in Table 3 were passed through a 20 mesh screen. The sieved materials were placed into a 500 cc plastic bottle and blended end over end with the remaining materials in Table 3. The powder blend was placed into the forming cavity, tamped, and activated with RF energy as described in Example 2 for approximately 2 to 5 seconds to form the orally disintegrating tablet and subsequently removed from the die platen.

TABLE 3

Powder Blend Formulation

| Ingredient | G/Batch | Mg/Tablet |
| --- | --- | --- |
| Dextrose Monohydrate | 283.04 | 255.0 |
| Polyethylene Glycol 8000[1] | 35.30 | 31.80 |
| Maltodextrin[2] | 70.71 | 63.70 |
| Yellow Colorant | 0.62 | 0.56 |
| Orange Flavor | 1.32 | 1.19 |
| Vanilla Flavor | 1.76 | 1.59 |
| Sucralose USP | 0.89 | 0.80 |
| Citric Acid Anhydrous USP | 6.36 | 5.73 |
| Total | 400.00 | 360.37 |

[1]Commercially available from Clariant PF in Rothausstr, Switzerland
[3]Commercially available from National Starch in Bridgewater, NJ Example 5

Manufacture of Orally Disintegrating Tablet Placebo Containing Erythritol

The placebo powder blend for an orally disintegrating tablet, containing the ingredients of Table 4, was manufactured as follows. The sucralose, yellow colorant, flavors, polyethylene glycol and maltodextrin from the formula in Table 4 were passed through a 20 mesh screen. The sieved materials were placed into a 500 cc plastic bottle and blended end over end with the remaining materials in Table 4. The powder blend was placed into the forming cavity, tamped, and activated with RF energy as described in Example 2 for approximately 2 to 5 seconds to form the orally disintegrating tablet and subsequently removed from the die platen.

TABLE 4

Placebo Powder Blend Formulation Containing Erythritol

| Ingredient | G/Batch | Mg/Tablet |
| --- | --- | --- |
| Erythritol Directly Compressible[3] | 212.28 | 255.0 |
| Polyethylene Glycol 8000[1] | 26.47 | 31.80 |
| Maltodextrin[2] | 53.03 | 63.70 |
| Yellow Colorant | 0.47 | 0.56 |
| Orange Flavor | 0.99 | 1.19 |
| Vanilla Flavor | 1.32 | 1.59 |
| Sucralose USP | 0.67 | 0.80 |
| Citric Acid Anhydrous USP | 4.77 | 5.73 |
| Total | 300.00 | 360.37 |

[1]Commercially available from Clariant PF in Rothausstr, Switzerland
[3]Commercially available from National Starch in Bridgewater, NJ
[4]Commercially available from Corn Products in Westchester, IL Example 6

Manufacture of a Comparative Compressed Chewable Placebo Tablet

The placebo powder blend for a comparative chewable placebo tablet, containing the ingredients of Table 5, was manufactured as follows. The sucralose, yellow color, and flavors were passed through a 20 mesh screen prior to blending. The sieved materials were blended with the remaining materials in the formula in Table 5 and added to a 500 cc plastic bottle and blended end over end for approximately 3 minutes and discharged. The tablets were compressed using two different compression forces as follows: Tablets (a) were compressed on a single station manual Carver press (commercially available from Carver Press Corporation in Wabash, Ind.) at 0.7 Metric tons (6.86 KiloNewtons) and Tablets (b) were compressed at 0.25 Metric tons (2.45 KiloNewtons). Tablets (b) were extremely friable and fragile given the low amount of pressure applied to the formulation.

TABLE 5

Placebo Powder Blend Formulation for Compressed Tablet

| Ingredient | G/Batch | Mg/Tablet |
| --- | --- | --- |
| Dextrose Monohydrate | 114.773 | 138.00 |
| Polyethylene Glycol 4000[1] | 41.584 | 50.00 |
| Maltodextrin[2] | 35.763 | 43.00 |
| Blue Colorant | 0.075 | 0.0907 |
| Yellow Colorant | 0.153 | 0.1842 |
| Vanilla Flavor | 1.830 | 2.20 |
| Sucralose USP | 1.248 | 1.50 |
| Mint Flavor[1] | 4.574 | 5.50 |
| Total | 200 | 240.47 |

[1]Commercially available from Clariant PF in Rothausstr, Switzerland
[3]Commercially available from National Starch in Bridgewater, NJ Example 7

Manufacture of a Comparative Compressed Chewable Containing Acetaminophen

The placebo powder blend for a chewable tablet, containing the ingredients of Table 6, was manufactured as follows. The sucralose, yellow color, flavors, and citric acid were passed through a 20 mesh screen prior to blending. The sieved materials were blended with the remaining materials in the formula in Table 6 and added to a 500 cc plastic bottle and blended end over end for approximately 3 minutes and discharged. The tablets were compressed using two different compression forces as follows: Tablets (a) were lightly compressed on a single station manual Carver press at 0.7 Metric tons (6.86 KiloNewtons) and Tablets (b) were compressed at 0.25 Metric tons (2.45 KiloNewtons). Tablets (b) were extremely friable and fragile given the low amount of pressure applied to the formulation.

TABLE 6

Powder Blend Formulation Containing Acetaminophen

| Ingredient | G/Batch | Mg/Tablet |
| --- | --- | --- |
| Dextrose Monohydrate | 32.284 | 94.00 |
| Acetaminophen (Coated)[3] | 29.989 | 87.32 |
| Polyethylene Glycol 4000[1] | 5.152 | 15.00 |
| Maltodextrin[2] | 20.607 | 60.00 |
| Yellow Colorant | 0.120 | 0.35 |
| Orange Flavor | 0.343 | 1.00 |
| Vanilla Flavor | 0.515 | 1.50 |
| Sucralose USP | 0.343 | 1.00 |
| Crosslinked Povidone[5] | 2.061 | 6.00 |
| Polyethylene Oxide (Grade WSR 303)[4] | 6.869 | 20.00 |
| Citric Acid USP Anhydrous | 1.717 | 5.00 |
| Total | 100 | 291.17 |

[1]Commercially available from Clariant PF in Rothausstr, Switzerland
[2]Commercially available from National Starch in Bridgewater, NJ
[3]Encapsulated Acetaminophen coated utilizing cellulose acetate and povidone, utilizing process outlined in U.S. Pat. No. 4,851,226 incorporated herein by reference
[4]Commercially available from the DOW Corporation in Midland, MI
[5]Commercially available as Kollidon CL-M from the BASF Corporation in Florham Park, NJ Example 8

Density Measurements of ODT and Compressed Tablets

Three tablets from each of Examples 3, 4, 5, 6, and 7 were measured to determine the density of compressed tablets and tablets produced utilizing the method of the present invention. The density was calculated utilizing the volume of a cylinder as calculated using the width and thickness of the tablet divided by the weight of individual tablets.

TABLE 8

Tablet Density Measurements

| Example | Weight (mg) | Diameter (mm) | Height (mm) | Volume (mm$^3$) | Density (mg/mm$^3$) |
| --- | --- | --- | --- | --- | --- |
| Example 3 (1) | 379 | 13.13 | 5.00 | 677.0 | 0.560 |
| Example 3 (2) | 403 | 13.10 | 4.97 | 669.9 | 0.602 |
| Example 3 (3) | 409 | 13.03 | 4.87 | 649.4 | 0.630 |
| Example 4 (1) | 347 | 12.90 | 4.85 | 633.9 | 0.547 |
| Example 4 (2) | 416 | 12.97 | 4.96 | 655.3 | 0.635 |
| Example 4 (3) | 398 | 13.06 | 4.95 | 663.1 | 0.600 |
| Example 5 (1) | 419 | 12.90 | 5.38 | 703.2 | 0.596 |
| Example 5 (2) | 397 | 13.15 | 5.32 | 722.5 | 0.549 |
| Example 5 (3) | 352 | 12.87 | 5.00 | 650.5 | 0.541 |
| Example 6a (1) | 399 | 11.18 | 3.32 | 325.9 | 1.220 |
| Example 6a (2) | 372 | 11.16 | 3.06 | 299.3 | 1.240 |
| Example 6a (3) | 391 | 11.18 | 3.25 | 319.0 | 1.230 |
| Example 6b (1) | 433 | 11.20 | 4.27 | 420.7 | 1.030 |
| Example 6b (2) | 442 | 11.22 | 4.35 | 430.1 | 1.030 |
| Example 6b (3) | 404 | 11.18 | 3.93 | 385.8 | 1.050 |
| Example 7a (1) | 364 | 11.20 | 3.26 | 321.2 | 1.130 |
| Example 7a (2) | 328 | 11.18 | 2.94 | 288.6 | 1.140 |
| Example 7a (3) | 404 | 11.17 | 3.65 | 357.7 | 1.130 |
| Example 7b (1) | 413 | 11.25 | 4.66 | 463.2 | 0.890 |
| Example 7b (2) | 451 | 11.21 | 5.00 | 493.5 | 0.910 |
| Example 7b (3) | 437 | 11.22 | 4.82 | 476.6 | 0.920 |

As is shown in table 8, the ODT tablets of the present invention (Examples 3, 4, and 5) has densities ranging from 0.541-0.635 mg/mm$^3$, while the comparative chewable tablets of Examples 6 and 7 had densities ranging from 0.890-1.240 mg/mm$^3$. The ODT tablets of the present invention, thus, had densities approximately half of that of the comparative examples.

Example 9

Disintegration Test Utilizing Texture Analyzer TA XT Plus

The following test was performed utilizing the Texture Analyzer TA XT Plus, commercially available from Texture Technologies in Scarsdale, N.Y. The texture Analyzer was equipped with a TA-55 probe, and set to a probe speed of 0.1 mm/sec. The individual tablet was placed into a 5 mm graduated cylinder, and placed onto the short axis. 20 grams of force was applied to the tablet via the 5 mm probe. The force was applied and at approx. 10 mL of de-ionized water at 25° C. was added to cover the tablet. The force was analyzed over time and the following tablets were analyzed: the tablets of Example 6a and the tablets of Example 3. The tablets of the present invention (Example 3) disintegrated immediately following the addition of the water as indicated by the probe distance, which increased from 0 mm to greater than 1 mm between 10 and 20 seconds. The tablets from Example 6a, which were representative of chewable tablets, disintegrated in 84.30 seconds from the addition of water as measured by the change in slope in the texture analyzer, where tablets of Example 3 were completely disintegrated in 6.99 seconds from the addition of water.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A machine for the production of a solid dosage form, said machine comprising:
   (a) a die platen having one or more forming cavities each having an inner wall, a first opening at a surface of one side of said die platen, and a second opening at a surface on a opposite side of said die platen;
   (b) one or more first forming tools each adapted to move into one of said cavities through the first opening of said forming cavity;
   (c) one or more second forming tools each adapted to move adjacent to one of said second openings or into one of said cavities through the second opening of said forming cavity;
   (d) at least one first RF electrode operably associated with said one or more first forming tools, said one or more second forming tools, or said inner wall of said one or more forming cavities; and
   (e) at least one second RF electrode operably associated with said one or more first forming tools, said one or more second forming tools, or said inner wall of said one or more forming cavities;
   wherein said machine is adapted to form said dosage form between one of said one or more first forming tools and one of said one or more second forming tools within one of said one or more forming cavities and wherein said first RF electrode and said second RF electrode are arranged within said machine such that when RF energy is conducted between said first RF electrode and said second RF electrode, said RF energy passes through a portion of said forming cavity adapted to form said dosage form.

2. A machine if claim 1, wherein said machine further comprises an RF energy source in communication with said first RF electrode and said second RF electrode.

3. A machine of claim 2, wherein said machine further comprises a feeder adapted to add powder blend to said one or more forming cavities.

4. A machine of claim 2, wherein said first RF electrode is operably associated with said one or more first forming tools, said second RF electrode is operably associated with said one or more second forming tools, and a portion of the inner wall of said forming cavity which is adapted to form said dosage form is insulative to said RF energy.

5. A machine of claim 4, wherein only a portion of a surface of said first forming tool that is adapted to contact said dosage form is operably associated with said first RF electrode.

6. A machine of claim 5, wherein said die platen comprises at least six of said forming cavities.

7. A machine of claim 6, wherein said machine further comprises a feeder adapted to add powder blends into said one or more forming cavities.

8. A machine of claim 5, wherein said machine further comprises a feeder adapted to add powder blends into said one or more forming cavities.

9. A machine of claim 4, wherein said die platen comprises at least six of said forming cavities.

10. A machine of claim 9, wherein said machine further comprises a feeder adapted to add powder blends into said one or more forming cavities.

11. A machine of claim 4, wherein said machine further comprises a feeder adapted to add powder blends into said one or more forming cavities.

12. A machine of claim 2, wherein said die platen comprises at least six of said forming cavities.

13. A machine of claim 12, wherein said machine further comprises a feeder adapted to add powder blends into said one or more forming cavities.

14. A machine of claim 1, wherein said first RF electrode is operably associated with said one or more first forming tools, said second RF electrode is operably associated with said one or more second forming tools, and a portion of the inner wall of said forming cavity which is adapted to form said dosage form is insulative to said RF energy.

15. A machine of claim 14, wherein said die platen comprises at least six of said forming cavities.

16. A machine of claim 15, wherein said machine further comprises a feeder adapted to add powder blends into said one or more forming cavities.

17. A machine of claim 14, wherein only a portion of a surface of said first forming tool that is adapted to contact said dosage form is operably associated with said first RF electrode.

18. A machine of claim 17, wherein said die platen comprises at least six of said forming cavities.

19. A machine of claim 18, wherein said machine further comprises a feeder adapted to add powder blends into said one or more forming cavities.

20. A machine of claim 17, wherein said machine further comprises a feeder adapted to add powder blends into said one or more forming cavities.

21. A machine of claim 14, wherein said machine further comprises a feeder adapted to add powder blends into said one or more forming cavities.

22. A machine of claim 1, wherein said first RF electrode is operably associated with said one or more first forming tools and second RF electrode is operably associated with the portion of said inner wall of said one or more forming cavities that is adapted to form said dosage form.

23. A machine of claim 1, wherein said first RF electrode is operably associated with a first portion of said inner wall of said one or more forming cavities that is adapted to form said dosage form and second RF electrode is operably associated with a second portion of said inner wall of said one or more forming cavities that is adapted to form said dosage form.

24. A machine of claim 1, wherein said one or more first forming tools and said one or more second forming tool are heated and/or the die platen is heated.

25. A machine of claim 1, wherein said machine further comprises a feeder adapted to add powder blends into said one or more forming cavities.

26. A machine of claim 1, wherein said die platen comprises at least six of said forming cavities.

27. A machine of claim 26, wherein said machine further comprises a feeder adapted to add powder blends into said one or more forming cavities.

* * * * *

UNITED STATES PATENT AND TRADEMARK OFFICE
CERTIFICATE OF CORRECTION

| | | |
|---|---|---|
| PATENT NO. | : 8,807,979 B2 | Page 1 of 1 |
| APPLICATION NO. | : 12/887569 | |
| DATED | : August 19, 2014 | |
| INVENTOR(S) | : Sowden et al. | |

It is certified that error appears in the above-identified patent and that said Letters Patent is hereby corrected as shown below:

In the Claims

--Column 27, line 42, Claim 2, the word "if" is incorrect, and should be replaced with the word "of".--

Signed and Sealed this
First Day of March, 2016

Michelle K. Lee
*Director of the United States Patent and Trademark Office*